US008594941B2

(12) United States Patent
Chandra et al.

(10) Patent No.: US 8,594,941 B2
(45) Date of Patent: *Nov. 26, 2013

(54) SYSTEM, METHOD AND APPARATUS FOR CAUSAL IMPLICATION ANALYSIS IN BIOLOGICAL NETWORKS

(75) Inventors: Dundee Navin Chandra, Framingham, MA (US); Maria Fatima Chandra, legal representative, Framingham, MA (US); Suresh Toby Segaran, Somerville, MA (US); David Kightley, York, ME (US); Justin Sun, Norwood, MA (US); Dexter Pratt, Reading, MA (US)

(73) Assignee: Selventa, Inc., Cambridge, MA (US)

( * ) Notice: Subject to any disclaimer, the term of this patent is extended or adjusted under 35 U.S.C. 154(b) by 785 days.

This patent is subject to a terminal disclaimer.

(21) Appl. No.: 10/992,973

(22) Filed: Nov. 19, 2004

(65) Prior Publication Data

US 2005/0165594 A1    Jul. 28, 2005

Related U.S. Application Data

(60) Provisional application No. 60/525,543, filed on Nov. 26, 2003.

(51) Int. Cl.
*G01N 33/50* (2006.01)

(52) U.S. Cl.
USPC ........................................................ 702/19

(58) Field of Classification Search
None
See application file for complete search history.

(56) References Cited

U.S. PATENT DOCUMENTS

| | | | | |
|---|---|---|---|---|
| 4,935,877 | A | 6/1990 | Koza | 364/513 |
| 5,136,686 | A | 8/1992 | Koza | 395/13 |
| 5,148,513 | A | 9/1992 | Koza et al. | 395/13 |
| 5,343,554 | A | 8/1994 | Koza et al. | 395/13 |
| 5,390,282 | A | 2/1995 | Koza et al. | 395/13 |
| 5,742,738 | A | 4/1998 | Koza et al. | 395/13 |
| 5,867,397 | A | 2/1999 | Koza et al. | 364/489 |
| 5,914,891 | A | 6/1999 | McAdams et al. | |
| 6,058,385 | A | 5/2000 | Koza et al. | 706/13 |
| 6,360,191 | B1 | 3/2002 | Koza et al. | 703/6 |
| 6,424,959 | B1 | 7/2002 | Bennett, III et al. | 706/13 |
| 6,532,453 | B1 | 3/2003 | Koza et al. | 706/13 |
| 6,564,194 | B1 | 5/2003 | Koza et al. | 706/13 |
| 6,594,587 | B2 | 7/2003 | Askenazi | 702/19 |
| 6,665,669 | B2 | 12/2003 | Han et al. | 707/6 |
| 6,741,986 | B2 | 5/2004 | Cho et al. | |
| 6,772,160 | B2 | 8/2004 | Cho et al. | |
| 6,983,227 | B1 * | 1/2006 | Thalhammer-Reyero | 703/2 |
| 2001/0016822 | A1 | 8/2001 | Bessette | 705/3 |
| 2001/0047353 | A1 | 11/2001 | Talib et al. | 707/3 |
| 2002/0002559 | A1 | 1/2002 | Busa | 707/104.1 |
| 2002/0049782 | A1 | 4/2002 | Herzenberg et al. | 707/500.1 |
| 2002/0123847 | A1 | 9/2002 | Askenazi | 702/20 |
| 2002/0198858 | A1 | 12/2002 | Stanley et al. | 706/50 |
| 2003/0033127 | A1 * | 2/2003 | Lett | 703/11 |
| 2003/0074516 | A1 | 4/2003 | Cho et al. | |
| 2003/0215786 | A1 * | 11/2003 | Hill et al. | 435/4 |
| 2003/0224363 | A1 | 12/2003 | Park et al. | |
| 2005/0038608 | A1 * | 2/2005 | Chandra et al. | 702/19 |

FOREIGN PATENT DOCUMENTS

| | | |
|---|---|---|
| EP | 1248231 | 10/2002 |
| WO | WO 02/11048 A2 | 2/2002 |
| WO | WO 02/093409 | 11/2002 |
| WO | WO-03/027262 | 4/2003 |
| WO | WO 03/067504 A2 | 8/2003 |
| WO | WO 03/082214 | 10/2003 |

OTHER PUBLICATIONS

Ideker et al. (Pacific Symposium on Biocomputing, Discovery of Regulatory Interactions Through Perturbation: Inference and Experiemental Design, 2000, No. 5, pp. 302-213).*
Shannon et al., (Genome Research, Cytoscape: A Software Environment for Integrated Models of Biomolecular Interaction Networks, 2003, No. 13: pp. 2498-2504).*
Sauro et al. (OMICS A Journal of Integrative Biology, Next Generation Simulation Tools: The Systems Biology Workbench and BioSPICE Integration, 2003, vol. 7, No. 4, pp. 353-370).*
Center for Development of Advanced Computing, "Workshop on Genetic Algorithms in Bioinformatics," http://www.cdacindia.com/html/ecents/bioinfo/genetic/genidx.asp, pp. 1-6 (printed Oct. 22, 2002).
Jansen, Ronald, "A Bayesian Networks Approach for Predicting Protein-Protein Interactiojns from Genomic Data," Science, vol. 302, pp. 449-453 (Oct. 17, 2003).
Karp, Peter D., "The EcoCyc Database," pp. 1-6 (Jan. 25, 2002).

(Continued)

*Primary Examiner* — Jason Sims
(74) *Attorney, Agent, or Firm* — David H. Judson

(57) ABSTRACT

Described are methods, systems and apparatus for hypothesizing a biological relationship in a biological system. A database of biological assertions is provided consisting of biological elements, relationships among the biological elements, and relationship descriptors characterizing the properties of the elements and relationships. A biological element may be selected from the database and a logical simulation may be performed within the biological database, from the selected biological element, through relationship descriptors, along a path defined by potentially causative biological elements to discern a biological element hypothetically responsible for the change in the selected biological element. The logical simulation may be either a backward logical simulation, performed upstream through the relationship descriptors to discern a hypothetical responsible biological element, or a forward logical simulation, performed downstream through the relationship descriptors to discern the extent to which the perturbation generates the observed change in the selected biological element.

23 Claims, 17 Drawing Sheets

(56) References Cited

OTHER PUBLICATIONS

Karp, Peter D., "Integrated Access to Metabolic and Genomic Data," pp. 1-32 (Apr. 1, 1996).
Karp, Peter D., "The MetaCyc Database," pp. 1-7 (Jan. 25, 2002).
Karp, Peter D., "Pathway Databases: A Case Study in Computational Symbolic Theories," Science, vol. 293, pp. 2040-2044 (Sep. 14, 2001).
Karp, Peter D., "The Pathway Tools Software," Bioinformatics, vol. 18 Suppl. 1 2002, pp. S1-S8 (2002).
Koza, John R., "Reverse Engineering and Automatic Synthesis of Metabolic Pathways From Observed Data Using Genetic Programming," pp. 1-53 (2000).
Koza, John R., "Reverse Engineering and Automatic Synthesis of Metabolic Pathways From Observed Data Using Genetic Programming," Symposium on Computational Discovery of Communicatable Knowledge, pp. 1-63 (Mar. 25, 2001).
Koza, John R., "Reverse Engineering and Automatic Synthesis of Metabolic Pathways From Observed Data Using Genetic Programming," Biomedical Informatics, pp. 1-12.
Rindfleisch, Thomas C., "Extracting Molecular Binding Relationships from Biomedical Text," pp. 188-195.
Stevens, Robert "Building a Reason-able Bioinformatics Ontology Using OIL," Department of Computer Science, University of Manchester, pp. 1-11.
Yen, John, "A Hybrid Approach to Modeling Metabolic Systems Using Genetic Algorithm and Simplex Method," pp. 1-42.
Yen, John, "Using Fuzzy Logic and a Hybrid Genetic Algorithm for Metabolic Modeling," pp. 1-6.
Goldberg, David E., "Genetic and Evolutionary Algorithms Come of Age," Communications of the ACM, vol. 37, No. 3, Mar. 1994, pp. 113-119.
van Helden, Jacques, et al., "Representing and Analysing Molecular and Cellular Function Using the Computer" Biol. Chem., vol. 381, pp. 921-935, Sep.-Oct. 2000.
Uetz, Peter, et al., "Visualization and Integration of Protein-Protein Interactions," in Golemis E (ed.) *Protein-Protein Interactions—A Molecular Cloning Manual*, Cold Spring Harbor Laboratory Press (available at: http://itgmv1.fzk.de/www/itg/uetz/publications/Visualization.pdf), 2002.
International Search Report; International Application No. PCT/US2004/039159; mailed on Aug. 31, 2005; 7 pgs.
Written Opinion; International Application No. PCT/US2004/039159; mailed on Aug. 31, 2005; 6 pgs.
International Search Report for PCT/US2003/030653, mailed Feb. 3, 2004.
International Search Report for International Application No. PCT/US/2005/00202 mailed from the International Searching Authority on Nov. 24, 2005.
Written Opinion of the International Searching Authority for International Application No. PCT/US/2005/00202 mailed from the International Searching Authority on Nov. 24, 2005.
International Search Report for PCT/US03/36857, mailed Mar. 9, 2005.
International Search Report for International Application No. PCT/US/2004/039159 mailed from the International Searching Authority on Aug. 31, 2005.
Written Opinion of the International Searching Authority for International Application No. PCT/US/2004/039159 mailed from the International Searching Authority on Aug. 31, 2005.
Barabasi et al., "Mean-field theory for scale-free random networks", Physica A, vol. 272 (1999), pp. 173-187.
Jeong et al., "Lethality and centrality in protein networks," Nature, vol. 411 (2001), pp. 41-42.
Jeong et al., "The large-scale organization of metabolic networks," Nature, vol. 407 (2007), pp. 651-654.

\* cited by examiner

| Treatment 1 | Treatment 2 | Treatment 3 | Predictions |
|---|---|---|---|
| Gene1 | Gene1 | Gene1 | Gene1 |
| Gene2 | Gene2 | Gene2 | Gene2 |
| Gene3 | Gene3 | Gene3 | Gene3 |
| Gene4 | Gene4 | Gene4 | Gene4 |
| Gene5 | Gene5 | Gene5 | Gene5 |
| Gene6 | Gene6 | Gene6 | Gene6 |
| Gene7 | Gene7 | Gene7 | Gene7 |
| Gene8 | Gene8 | Gene8 | Gene8 |
| Gene9 | Gene9 | Gene9 | Gene9 |

FIG. 15

Run backward simulation from gene expression results to get genes whose activity may explain results
Filter by votes and by knowledge of system
Save list of genes as backsim results
Retrieve gene expression experimental results
Store upregulated genes in upTargets list
Store downregulated genes in downTargets list
Run forward simulation using backsim results to get predicted changes in system
Filter predicted to only have gene expression nodes
Sort resulting genes by total positive and total negative votes (TPV and TNV) into following categories
   TPV-TNV > 0: predicted to be upregulated
      If in upTargets: correct prediction
      If in downTargets: opposite of prediction
      If not in either: predicted not observed
   TPV-TNV < 0: predicted to be upregulated
      If in downTargets: correct prediction
      If in upTargets: opposite of prediction
      If not in either: predicted not observed
   Else no net change
Now go through upTargets and downTargets and put genes not in prediction results into observed not predicted category
Output the following categories, display as pie charts or histograms
   Correctly predicted count
   Opposite predicted count
   Predicted not observed count
   Observed not predicted count
   No net change count

FIG. 16

SYSTEM, METHOD AND APPARATUS FOR CAUSAL IMPLICATION ANALYSIS IN BIOLOGICAL NETWORKS

RELATED APPLICATIONS

This application claims the benefit of U.S. provisional application No. 60/525,543, entitled "System, Method and Apparatus for Causal Implication Analysis in Biological Networks," filed Nov. 26, 2003, the disclosure of which is incorporated by reference herein.

TECHNICAL FIELD

The invention relates to methods, systems and apparatus for analyzing causal implications in biological networks, and more particularly, to methods, systems and apparatus for hypothesizing a biological relationship in a biological system, for simulating a perturbation within a biological system, and for hypothesizing a relationship between two biological elements by performing a logical simulation within a database of biological knowledge.

BACKGROUND

The amount of biological information generated in the today's world is increasing dramatically. It is estimated that the amount of information now doubles every four to five years. Because of the large amount of information that must be processed and analyzed, traditional methods of discerning and understanding the meaning of information, especially in the life science-related areas, are breaking down. Statistical techniques, while useful, do not provide a biologically motivated explanation of how things work. The present invention takes a causative approach (rather than correlative) at understanding biological effects.

To form an effective understanding of a biological system, a life science researcher must synthesize information from many sources. Understanding biological systems is made more difficult by the interdisciplinary nature of the life sciences. Forming an understanding of a biological system may require in-depth knowledge of genetics, cell biology, biochemistry, medicine, and many other fields. Understanding a system may require that information of many different types be combined. Life science information may include material on basic chemistry, proteins, cells, tissues, and effects on organisms or population—all of which may be interrelated. These interrelations may be complex, poorly understood, or hidden.

There are ongoing attempts to produce electronic models of biological systems. These involve compilation and organization of enormous amounts of data, and construction of a system that can operate on the data to simulate the behavior of a biological system. Because of the complexity of biology, and the sheer numbers of data, the construction of such a system can take hundreds of man years and multiple tens of millions of dollars. Furthermore, those seeking new insights and new knowledge in the life sciences are presented with the ever more difficult task of connecting the right data from mountains of information gleaned from vastly different sources. Companies willing to invest such resources so far have been unsuccessful in compiling models of real utility which aid researchers significantly in advancing biological knowledge. Thus, to the extent current systems of generating and recording life science data have been developed to permit knowledge processing and analysis, they are clearly far from optimal, and significant new efficiencies are needed.

More specifically, what is needed in the art is a way to assemble vast amounts of diverse life science-related knowledge, and to discern from it insightful and meaningful new biological relationships, pathways, causes and effects, and other insights with efficiency and ease.

SUMMARY OF THE INVENTION

In accordance with the invention, it has been realized that a key to providing useful and manageable biological knowledge bases that are capable of effectively modeling biological systems is to provide means for rapidly and efficiently analyzing relationships between biological elements. A biological knowledge base containing assertions regarding the biological elements and the many possible relationships between the elements can be analyzed to facilitate understanding and revelation of hidden interactions and relationships in biological systems, i.e., to produce new biological knowledge. This in turn permits the generation of new hypotheses concerning biological pathways based on the new biological knowledge, and permits the user to design and conduct biological experiments using biomolecules, cells, animal models, or a clinical trial to validate or refute a hypothesis.

The invention thus provides a novel method, apparatus, and tool set which can be applied to a global knowledge base. The tools and methods enable efficient execution of discovery projects in the life sciences-related fields. The invention permits one to address any biological topic, no matter how obscure or esoteric, provided there are at least some assertions in a global knowledge base relevant to the topic. Assertions represent facts relating existing objects in a system, or a fact about one object in the system and some literal value, or any combination thereof.

The invention provides methods of hypothesizing a biological relationship in a biological system using a database of biological assertions, or means, such as a user interface, for accessing such a knowledge base. The knowledge base includes a multiplicity of nodes representative of biological elements and relationship descriptors describing relationships among the nodes and characterizing properties of the nodes and relationships. A preferred knowledge base is disclosed in co-pending, co-owned U.S. patent application Ser. No. 10/644,582, the disclosure of which is incorporated by reference herein.

The invention provides methods for discovering new biological knowledge. The methods include providing a database of biological assertions comprising a multiplicity of nodes representative of biological elements and relationship descriptors describing relationships between nodes and characterizing properties of the nodes and relationships.

The methods further include selecting a node in the database for analysis. In some embodiments, the selected node is known from experimental observation to correspond to a biological element which increases in number or concentration, decreases in number or concentration, appears within, or disappears from a real biological system when it is perturbed.

The effect of perturbing a selected node, in another embodiment, is not known to correspond to a biological element, but may be investigated using the system by representing the specific perturbation and then reasoning about the effects based on the biological knowledge represented in the system. The selected node is perturbed by specifying an increase in concentration or number, stimulation of activity, an effective decrease in concentration or number, inhibition of activity, or the appearance or disappearance of the selected node. In another embodiment, a pair or multiplicity of nodes may be selected from the database and perturbed.

The invention provides methods for performing logical simulation within a biological knowledge base. Logical simulation includes backward logical simulations, which proceeds from a selected node upstream through a path of relationship descriptors to discern a node which is hypothetically responsible for the experimentally observed changes in the biological system. In short, this computation answers the question "What could have caused the observed change?" Logical simulation also includes forward logical simulations, which travel from the target node downstream through a path of relationship descriptors to discern the extent to which a perturbation to the target node causes experimentally observed changes in the biological system.

The invention provides methods for performing a logical simulation on a hypothetical perturbation. One or more nodes may be selected and specified as perturbed, regardless of whether they are observed in an actual experiment. Backward logical simulation on the hypothetical perturbation includes backward logical simulations, which travel directly or indirectly from the target node upstream through a path of relationship descriptors to discern a hypothesis or node potentially explanatory of a cause of the specified change in the biological system. Forward logical simulation on the hypothetical perturbation identifies the nodes and relationship descriptors which would potentially be perturbed due to the hypothetical perturbation. The logical simulation also includes forward logical simulations, which travel directly or indirectly from the target node downstream through a path of relationship descriptors to discern a hypothesis or node potentially explanatory of an effect of the specified change on the biological system.

The invention provides methods for performing a logical simulation between at least two groups of selected nodes. The logical simulation travels through a path of relationship descriptors containing at least one potentially causative node or at least one potential effector node to discern a pathway hypothetically linking the target nodes. The set of these paths, derived in either manner, comprise the set of all possible explanations for perturbations of the target nodes which could hypothetically be caused due to perturbations of the source nodes.

In various embodiments, the invention includes method steps, applications, and devices wherein the database contains noisy data, erroneous data, or omits nodes representing structures, processes, or networks present in the real biological system.

In various embodiments, the invention includes method steps, applications, and devices wherein a probability algorithm is applied to plural hypotheses to assess which hypothetical relationship has the highest probability of representing real biology.

In various embodiments, the invention includes method steps, applications, and devices wherein the biological system is a mammalian biological system. The method further comprises determining the identity of a second hypothetically responsible node upstream of the hypothetically responsible node. Perturbation of the biological entity represented by the second node is predicted to induce a predetermined change in the biological system upon inhibition or stimulation.

In various embodiments, the invention includes method steps, applications, and devices for conducting an experiment on a biological specimen to determine if the hypothetical changes predicted by logical simulation correspond to the biologically observed change. The invention includes performing an experiment on a biological specimen to attempt to induce the observed change.

In various embodiments, the invention includes method steps, applications, and devices wherein the biological system being analyzed is a mammalian biological system that is perturbed from stasis. The perturbation is induced by a disease, toxicity, environmental exposure, abnormality, morbidity, aging, or another stimulus.

In various embodiments, the invention includes method steps, applications, and devices for determining the state of a group of biological entities represented by nodes in the system which are reproducibly associated with the biological state of the mammal which can act as a marker set characteristic of the biological state.

In various embodiments, nodes represent enzymes, cofactors, enzyme substrates, enzyme inhibitors, DNAs, RNAs, transcription regulators, DNA activators, DNA repressors, signaling molecules, trans membrane molecules, transport molecules, sequestering molecules, regulatory molecules, hormones, cytokines, chemokines, antibodies, structural molecules, metabolites, vitamins, toxins, nutrients, minerals, agonists, antagonists, ligands, receptors, or combinations thereof. In other embodiments, nodes represent protons, gas molecules, organic molecules, amino acids, peptides, protein domains, proteins, glycoproteins, nucleotides, oligonucleotides, polysaccharides, lipids, glycolipids, or combinations thereof. In further embodiments, nodes comprise cells, tissues, or organs, or drug candidate molecules.

In various embodiments, biological information represented by nodes and relationship descriptors may include experimental data, knowledge from the literature, patient data, clinical trial data, compliance data, chemical data, medical data, or hypothesized data. In other embodiments, biological information represented may include facts about of a molecule, biological structure, physiological condition, trait, phenotype, or biological process.

In various embodiments, relationship descriptors represent the condition, location, source, amount, or substructure of a molecule. Relationship descriptors also may be used to represent biological structure, physiological condition, trait, phenotype, biological process, clinical data, medical data, or disease data and chemistry. A particular relationship descriptor also corresponds to an epistemological relationship between a pair of nodes. Relationship descriptors are represented as case frames.

In various embodiments, the database contains at least 1,000 nodes, 5,000 nodes, 10,000 nodes, 50,000 nodes, or 100,000 nodes.

In various embodiments, the new biological knowledge produced by the method includes predictions of physiological behavior in humans, for example, from analysis of experiments conducted on animals, such as drug efficacy and/or toxicity, or the discovery of biomarkers indicative of the prognosis, diagnosis, drug susceptibility, drug toxicity, severity, or stage of disease.

The invention provides computing devices for analyzing a biological knowledge base and for discovering new biological knowledge. The computing devices include means for accessing an electronic database of biological assertions comprising a multiplicity of nodes representative of biological elements, relationship descriptors representing relationships between nodes and characterizing the nodes and relationships, and a user interface for specifying biological elements or perturbations which will be analyzed by the device. The devices also include a computer application to perform a logical simulation of a perturbation to a selected biological element or relationship, to analyze the source or effects of the perturbation, and to assess the probability that the simulation generated pathway represents real biology.

The invention also provides articles of manufacture having a computer-readable program carrier with computer-readable instructions embodied thereon for performing the methods and systems described above.

The foregoing and other features and advantages of the present invention, as well as the invention itself, will be more fully understood from the description, drawings, and claims which follow.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which:

FIG. 15 shows an illustrative example of a visualization technique in accordance with the present invention that is based on a forward simulation that compares predicted outcomes with actual laboratory data.

FIG. 16 shows an example of an algorithm for use in validating a biological model by comparing predicted to actual results in accordance with the invention.

DESCRIPTION

Figure 1:
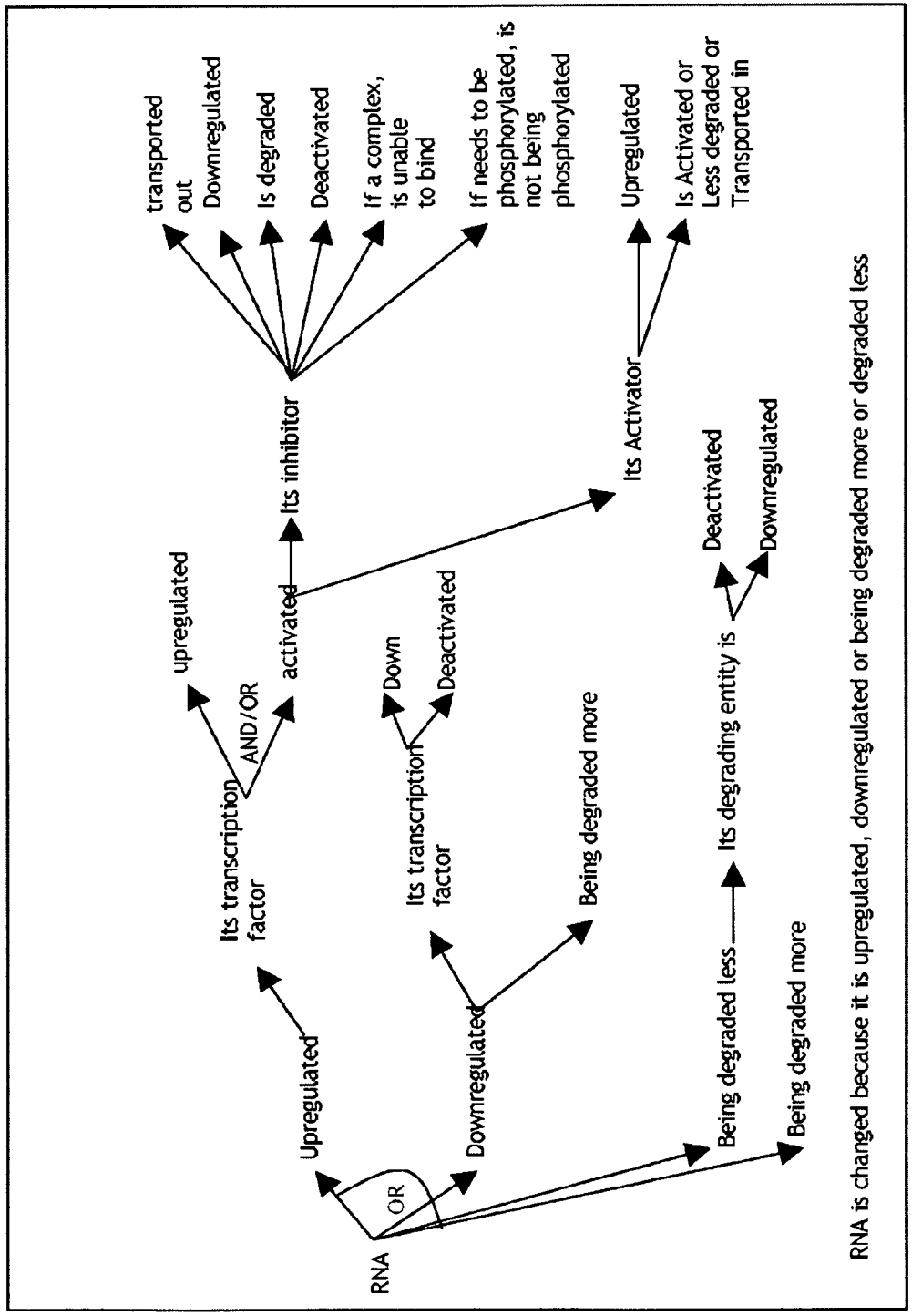
FIG. 1 is an exemplary causal tree showing inference paths for upstream causes starting with a change in mRNA levels for a particular gene in accordance with an illustrative embodiment of the invention.

To implement the present invention, a global knowledge base, or central database, is structured to comprise a multiplicity of nodes and relationship descriptors. Nodes represent elements of biological systems, both physical and functional, and include such things, for example, as specific organs, tissues, cells, organelles, cell compartments, membranes, proteins, DNAs, RNAs, small molecules, drugs, and metabolites. The relationship descriptors are data entries representing interrelations between nodes or associating additional information with nodes. Relationship descriptors connecting nodes may be thought of as "verbs" specifying the nature of a relationship between the represented biological entities. These may also be referred to as "case frames". Relationship descriptors may be used to represent additional information about the biological entity represented by a node, including but not limited to, recording the species or organ where a specific protein is found, identifying the journal where some datum was reported, notation of tertiary structural information about a specific protein, notation that some protein is elevated in patients with hypertension, etc. There are significantly more relationship descriptors in the knowledge base than there are nodes. Each node may have a plurality of relationship descriptors defining multiple attributes of that node.

Nodes may represent, by way of non-limiting examples, biological molecules including proteins, small molecules, ions, genes, ESTs, RNA, DNA, transcription factors, metabolites, ligands, trans-membrane proteins, transport molecules, sequestering molecules, regulatory molecules, hormones, cytokines, chemokines, histones, antibodies, structural molecules, metabolites, vitamins, toxins, nutrients, minerals, agonists, antagonists, ligands, or receptors. The nodes may represent drug substances, drug candidate compounds, antisense molecules, RNA, RNAi, shRNA, dsRNA, or chemogenomic or chemoproteomic probes. Viewed from a chemistry perspective, the nodes may represent protons, gas molecules, small organic molecules, amino acids, peptides, protein domains, proteins, glycoproteins, nucleotides, oligonucleotides, polysaccharides, lipids or glycolipids. Proceeding to higher order models, the nodes may represent protein complexes, protein-nucleotide complexes such as ribosomes, cell compartments, organelles, or membranes. From a structural perspective, they may represent various nanostructures such as filaments, intracellular lipid bilayers, cell membranes, lipid rafts, cell adhesion molecules, tissue barriers and semipermeable membranes, collagen structures, mineralized structures, or connective tissues. At still higher orders, the nodes represent cells, tissues, organs or other anatomical structures. For example, a model of the immune system might include nodes representing immunoglobulins, cytokines, various leucocytes, bone marrow, thymus, lymph nodes, and spleen. In simulating clinical trials the nodes may represent, for example, individuals, their clinical prognosis or presenting symptoms, drugs, drug dosage levels, and clinical end points. In simulating epidemiology, the nodes may represent, for example, individuals, their symptoms, physiological or health characteristics, their exposure to environmental factors, substances they ingest, and disease diagnoses. Nodes may also represent ions, physiological processes, diseases, disease processes, translocations, reactions, molecular complexes, cellular components, cells, anatomical parts, tissues, cell lines, and protein domains.

Relationship Descriptors

Relationship descriptors represent biological relationships between biological entities represented by nodes and contain each fact within a knowledge base. Relationship descriptors represent facts relating existing objects in a system, or a fact about one object in the system and some literal value, or any combination thereof. In various embodiments, relationship descriptors may represent knowledge such as RNA, proteomic, metabolite, or clinical knowledge from sources such as scientific publications, patient data, clinical trial data, compliance data, chemical data, medical data, hypothesized data, or data from biological databases.

Relationship descriptors may represent biological relationships between biological entities represented by nodes and include, but are not limited to, non-covalent binding, adherence, covalent modification, multi-molecular interactions (complexes), cleavage of a covalent bond, conversion, transport, change in state, catalysis, activation, stimulation, agonism, antagonism, up regulation, repression, inhibition, down regulation, expression, post-transcriptional modification, post-translational modification, internalization, degradation, control, regulation, chemo-attraction, phosphorylation, acetylation, dephosphorylation, deacetylation, transportation, and transformation.

One aspect of a relation descriptor is its attribution. Each relationship descriptor may have a multiplicity of attributions, characterizing multiple properties of the node or relationship. An attribution represents the source of the relationship, such as a scientific article, an abstract (e.g., Medline or PubMed), a book chapter, conference proceedings, a personal communication, or an internal memorandum. Another attribution of a relationship descriptor is its biological context. Relationship descriptors associated with a specific biological context may be selected. Biological context refers to, for example, species, tissue, body part, cell line, tumor, disease, sample, virus, organism, developmental stage, or any combination of the above. A further attribute of a relationship descriptor is its trust score, a measure of the level of confidence that the relationship descriptor reflects truly representative, real biology and is reproducible. Relationship descriptors can also be selected on the basis of a trust score. A minimum threshold is set and any relationships meeting or exceeding the threshold are selected. Additionally, seemingly identical relationship descriptors, containing the same nodes and relationship, may have different attributes, such as source, biological context, or certainty value, distinguishing the seemingly identical relationship descriptors.

Subsets of a knowledge base can also be made using specifications that define a complex pattern of relationships between nodes. All the sets of nodes and relationship descriptors which meet the criteria of the pattern embody the subset. In one embodiment, a search algorithm can filter the knowledge base to generate a list of biological entities that satisfy the stated pattern. For example, a structure search can be used to generate the subset of all reactions that have a product which is phosphorylated and whose catalyst is a molecular complex. This search will find all phosphorylation reactions that are catalyzed by a molecular complex, while avoiding phosphorylation reactions that are catalyzed by a single protein.

A preferred form of relationship descriptors for use in the invention are case frames extracted from the representation structure which permit instantiation and generalization of the models to a variety of different life science systems or other systems. Case frames are described in detail in co-pending, co-owned U.S. patent application Ser. No. 10/644,582, the disclosure of which is incorporated by reference herein. Relationship descriptors may comprise quantitative functions such as differential equations representing possible quantitative relationships between pairs of nodes which may be used to refine the network further. Relationship descriptors may also comprise qualitative features that either cannot be measured or described easily in an analytical or quantitative manner, or because of insufficient knowledge of a system in general or the feature itself, it is impossible to be described otherwise.

A knowledge base represents a hypothesis explaining the operation of systems, i.e., capable of producing, upon simulation, predicted data that matches the actual data that serves as the fitness criteria. The hypothesis can be tested with further experiments conducted, combined with other models or networks, refined, verified, reproduced, modified, perfected, corrected, or expanded with new nodes and new relationships based on manual or computer aided analysis of new data, and used productively as a biological knowledge base. Models of portions of a physiological pathway, or sub-networks in a cell compartment, cell, organism, population, or ecology may be combined into a consolidated model by connecting one or more nodes in one model to one or more nodes in another.

Pathfinding

Pathfinding algorithms including radial, shortest path, and all paths pathfinding. Radial pathfinding is useful to discover how one biological entity is functionally or structurally connected to other biological entities. For example, if a given cell contains a mutant form of P53, one may want to discover its effect on molecules upstream or downstream from the mutant gene product. An algorithm for discovering this information can start from a particular node and find all nodes that are connected to the node for a predetermined number of steps removed from the node. If directionality is important (e.g., as in reactions), the algorithm can be instructed to follow links only in the direction indicated by the pathfinding criteria. Radial pathfinding can be applied in several steps. For example, a two-step radial pathfinding search will involve starting from a node, finding its immediate connected nodes, and then finding the immediate connected nodes of those nodes. This process can be applied to as many steps as needed. This analysis may be used to determine and predict the expected changes of perturbing a given node. This analysis may be displayed to the user to elucidate how a change might propagate through the knowledge base, and thereby to discover its real effect on a biological system. An example of a causal tree as applied to RNA changes is shown in FIG. 1.

Figure 2:
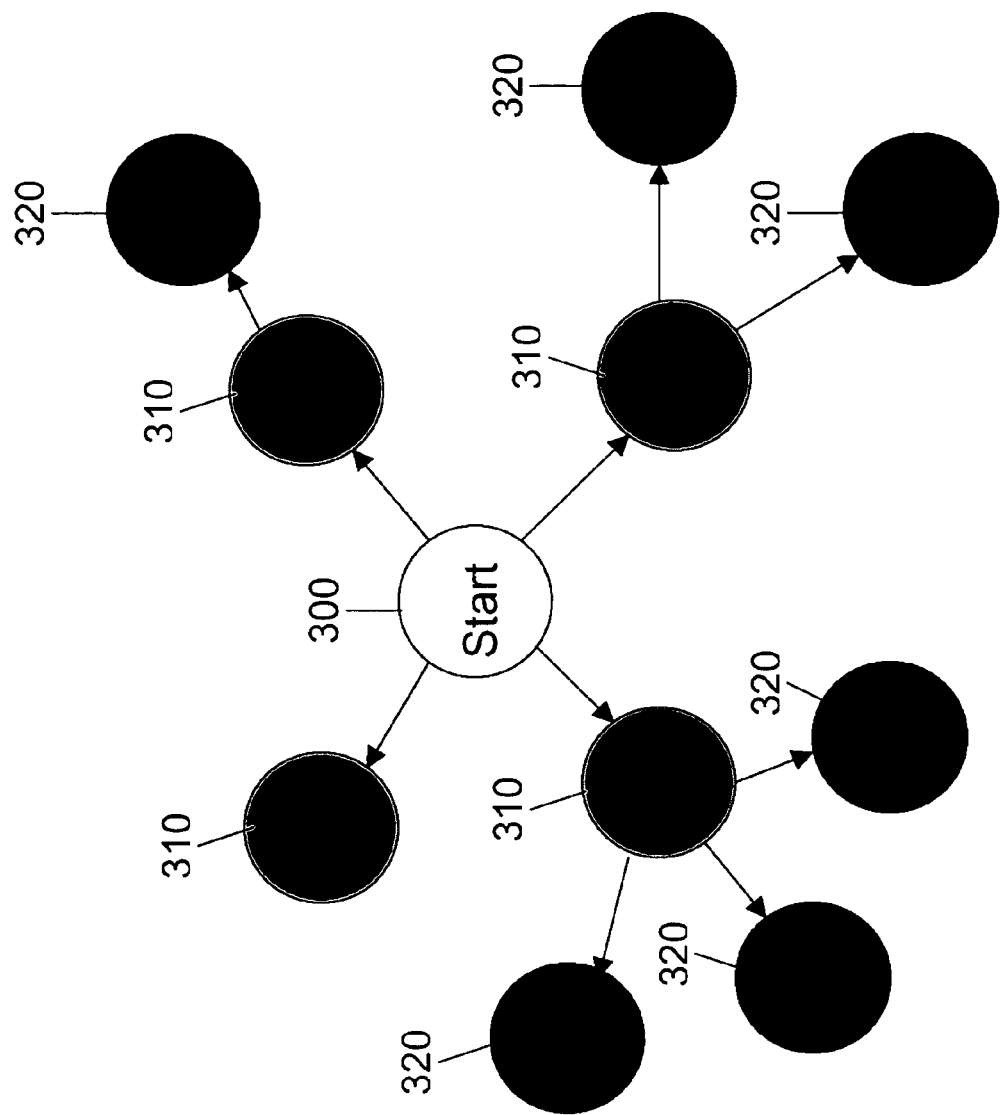
FIG. 2 shows a knowledge assembly graph in accordance with an illustrative embodiment of the invention.

FIG. 2 shows an example of the progression of a two-step radial pathfinding search starting from a specified start node 300. In the first step of the search, connected nodes 310 are found. In the second step of the search, connected nodes 320 are found. The result of this radial pathfinding search is the combination of all nodes and assertions as shown in the FIG. 2. A pathfinding search optionally can be configured to follow only specific descriptors, to ignore certain nodes that may be ubiquitous or uninformative, or to stop finding new nodes when certain nodes are encountered.

In large biological networks, there usually are multiple paths between any two entities. In a given analysis, it may be useful to determine the shortest path between two nodes, or to find all paths between two nodes. An algorithm for determining the shortest path in a network starts by performing a breadth-first radial pathfinding from each of the two nodes between which the shortest path is sought. Once a common node is found, the path is published as the shortest path between the nodes. To find all pathways, the algorithm can continue to pathfind radially from each node, identifying additional common nodes. In order to determine the pathways among several nodes, the algorithm discussed above can be run until all pathways between each pair of nodes are found. In this technique, one starts a radial pathfinding search from each one of the start nodes. Then, the paths being followed are recorded in every radial search. The union of all paths from the start nodes to the target nodes is the result of this algorithm. As this approach tends to increase exponentially in the number of pathways and nodes, the algorithm may be limited to follow a pre-designated number of steps. For example, a three-step search will only generate all pathways that exist between the given origin nodes by doing a three-step radial search out from each node. The results of this pathway algorithm can be displayed, for example as a sorted list of pathways starting from the shortest or largest, or as a merged graph.

Figure 3:
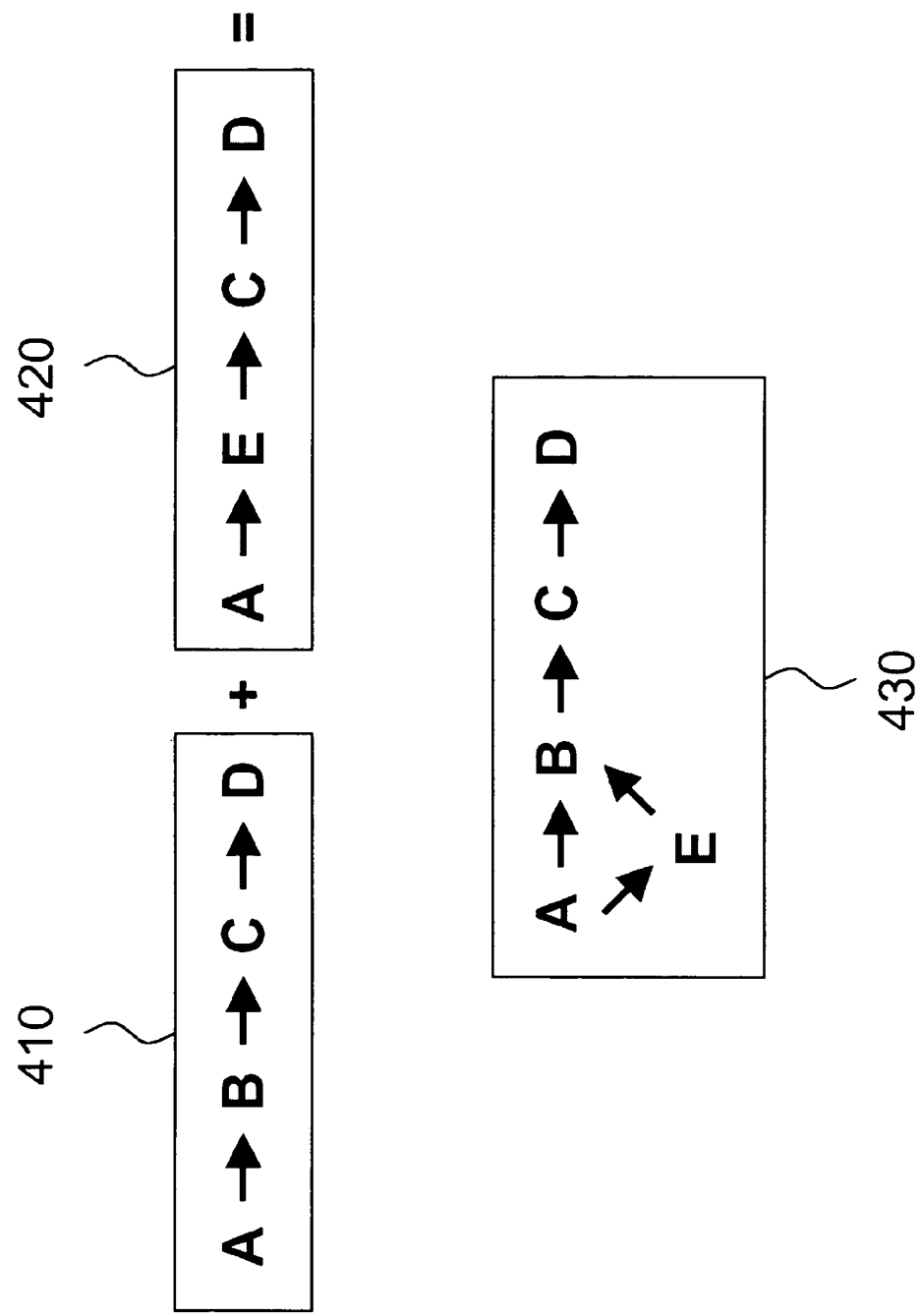
FIG. 3 shows the merger of two pathways in accordance with an illustrative embodiment of the invention.
Figure 4:
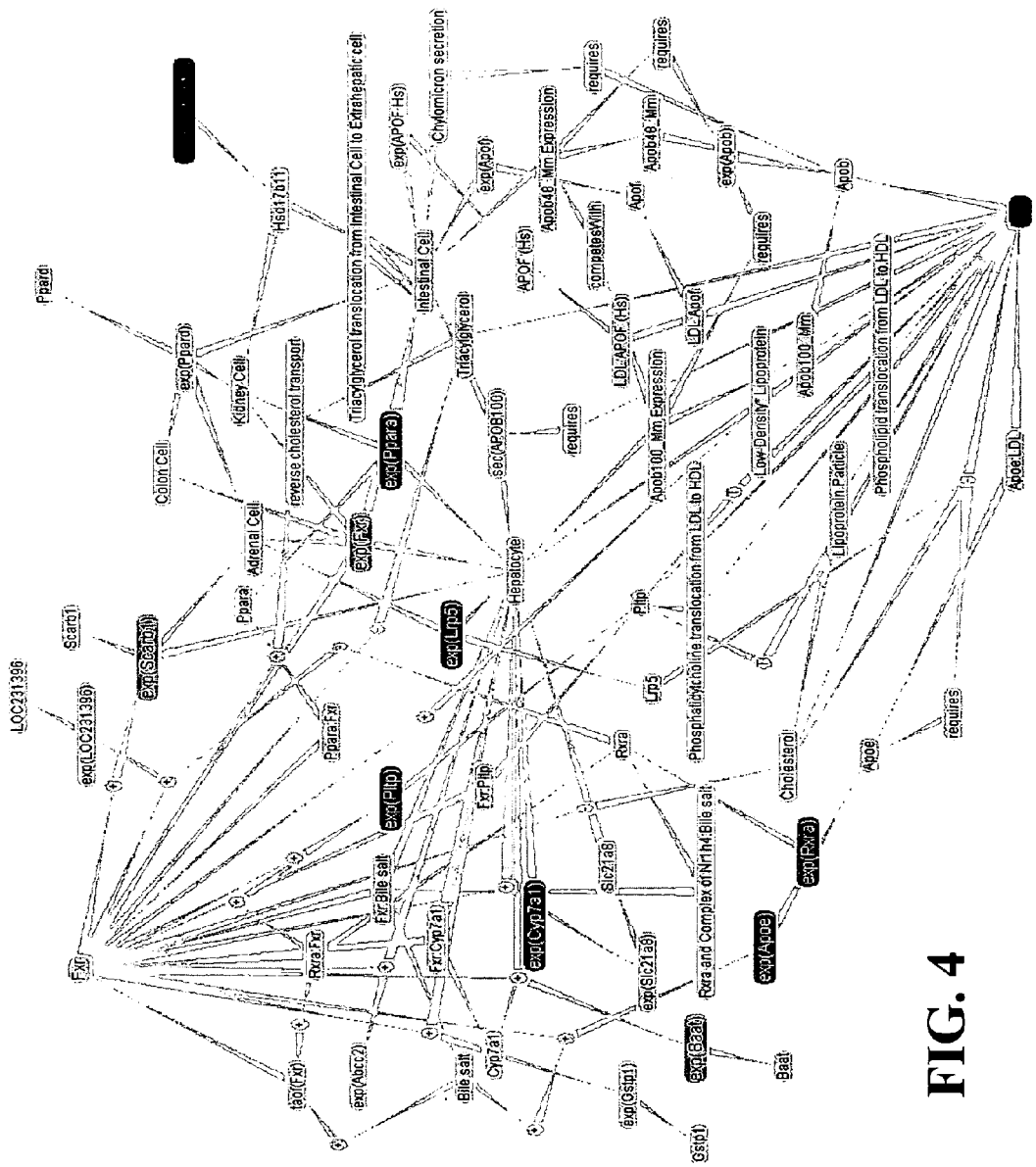
FIG. 4 shows a knowledge graph in accordance with an illustrative embodiment of the invention.

A merged graph is generated by merging together all of the pathways traversed up to a specific length in the case of a radial search or by merging the set of pathways that link any of the source nodes to any of the target nodes. This is accomplished by merging two pathways at a time, until only a single graph containing all nodes and assertions emerges. An example of merging two pathways involves taking all common nodes and assertions and merging them into combined pathway as shown in FIG. 3. In this diagram, since nodes A, B, and D are shared between pathway 410 and pathway 420, these nodes are represented only once in the combined pathway 430. Node B occurs in pathway 410 and node E occurs in pathway 420, and they are also represented in the combined pathway 430. FIG. 4 shows the result of merging all pathways into a single graph based on a radial pathway search between a start node "FXR" (in the upper left-hand corner of the diagram) and a target node "LDL" (in the lower right-hand corner of the diagram). This type of analysis permits study of the implications of observed changes in gene expression studies or changes in concentrations of proteins and metabolites. The analysis is used to show how the changed entities relate to one another so one can discern the dependent changes and find changes that are central to the experiment at hand.

Figure 5:
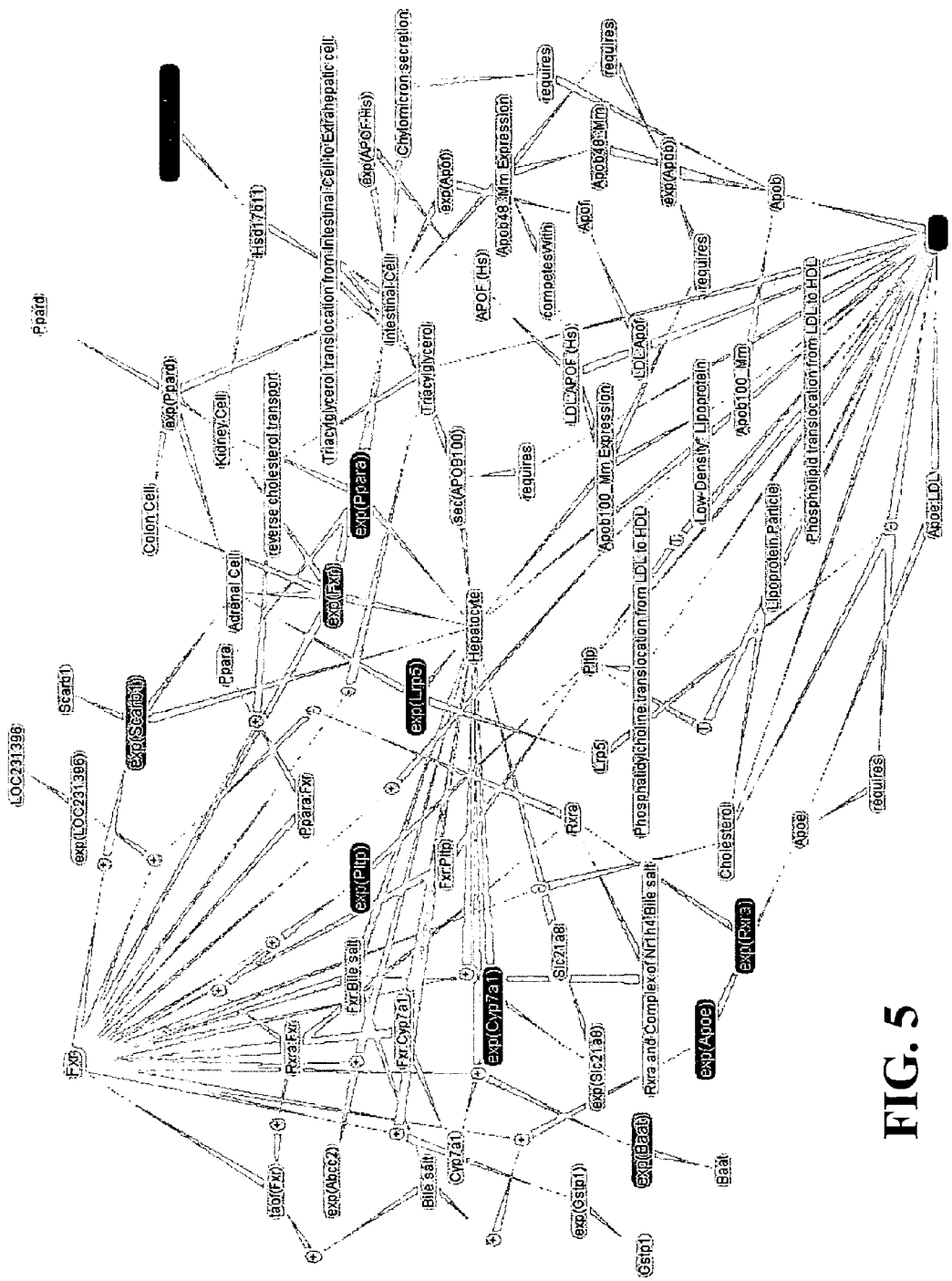
FIG. 5 shows a knowledge graph in accordance with an illustrative embodiment of the invention.
Figure 6:
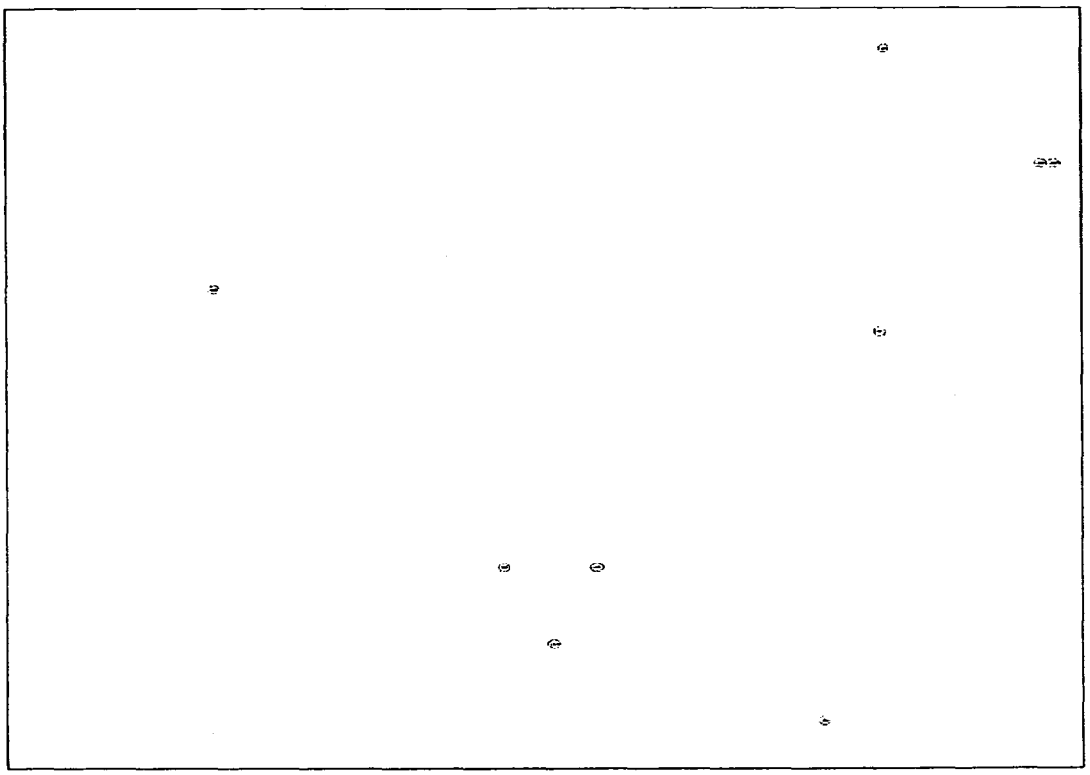
FIGS. 6-11 show the iterative steps of generation of a causal tree in accordance with an illustrative embodiment of the invention.
Figure 7:
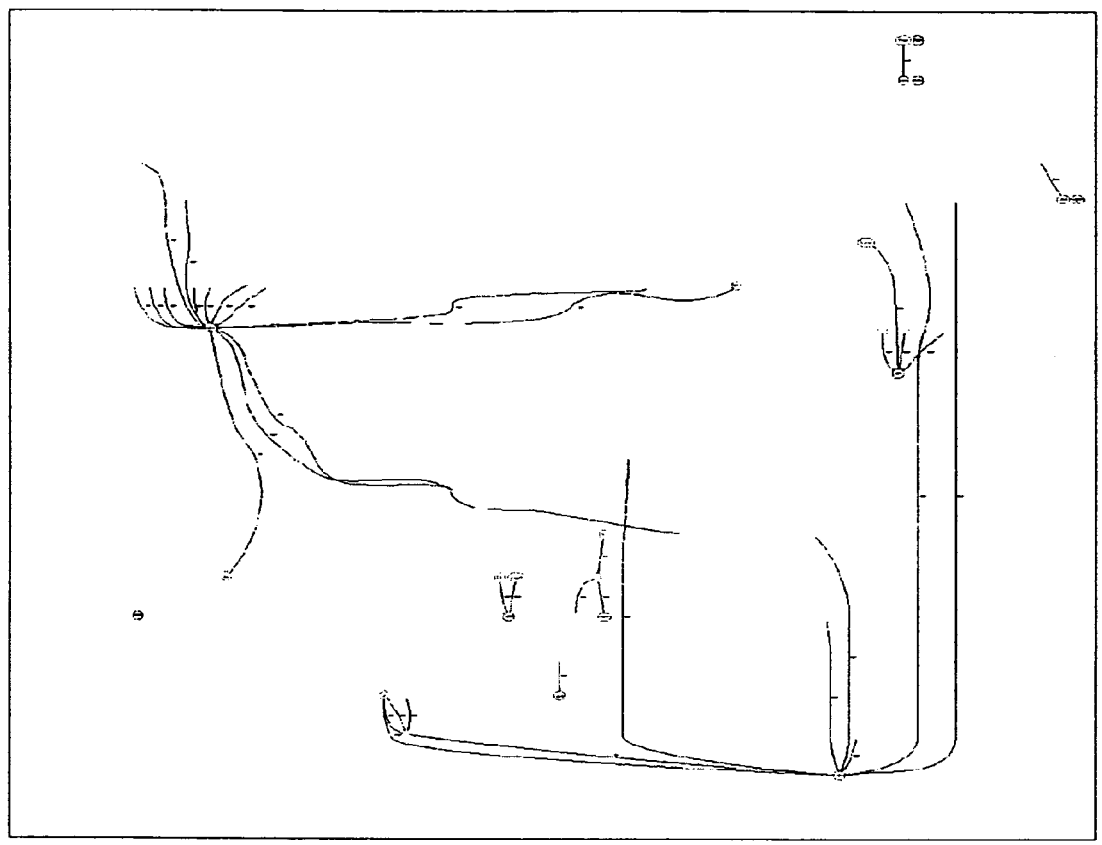
Figure 8:
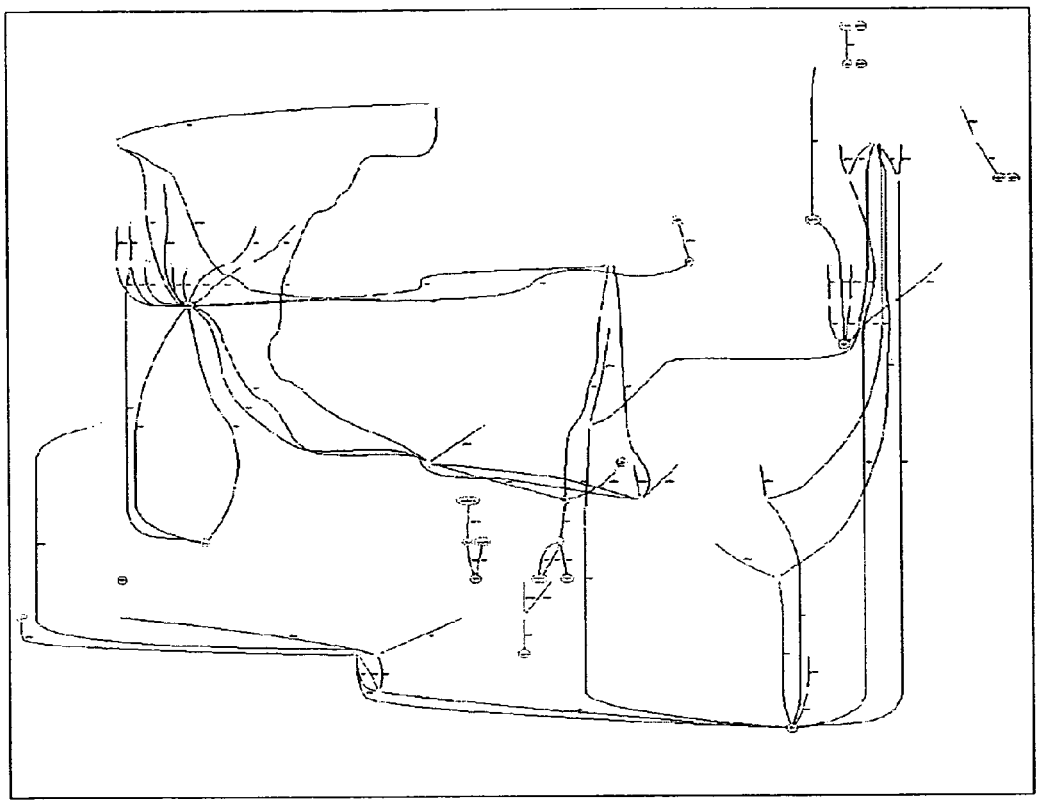
Figure 9:
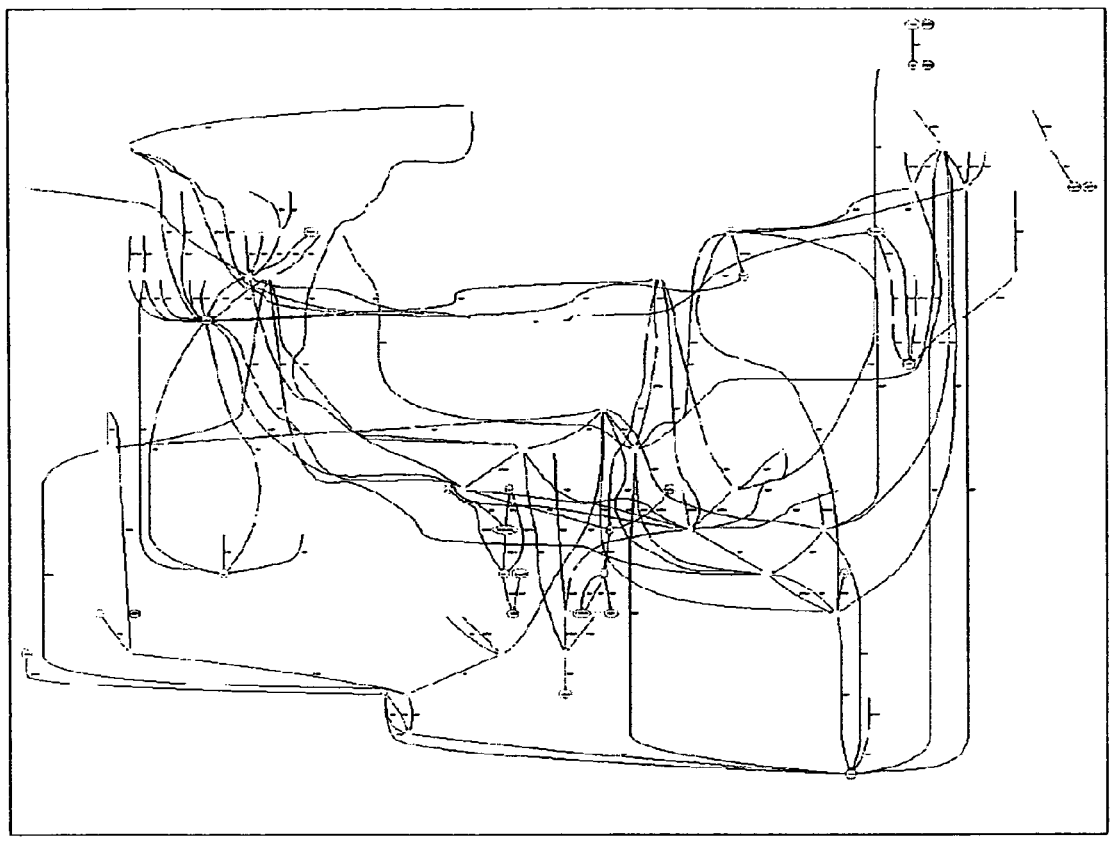
Figure 10:
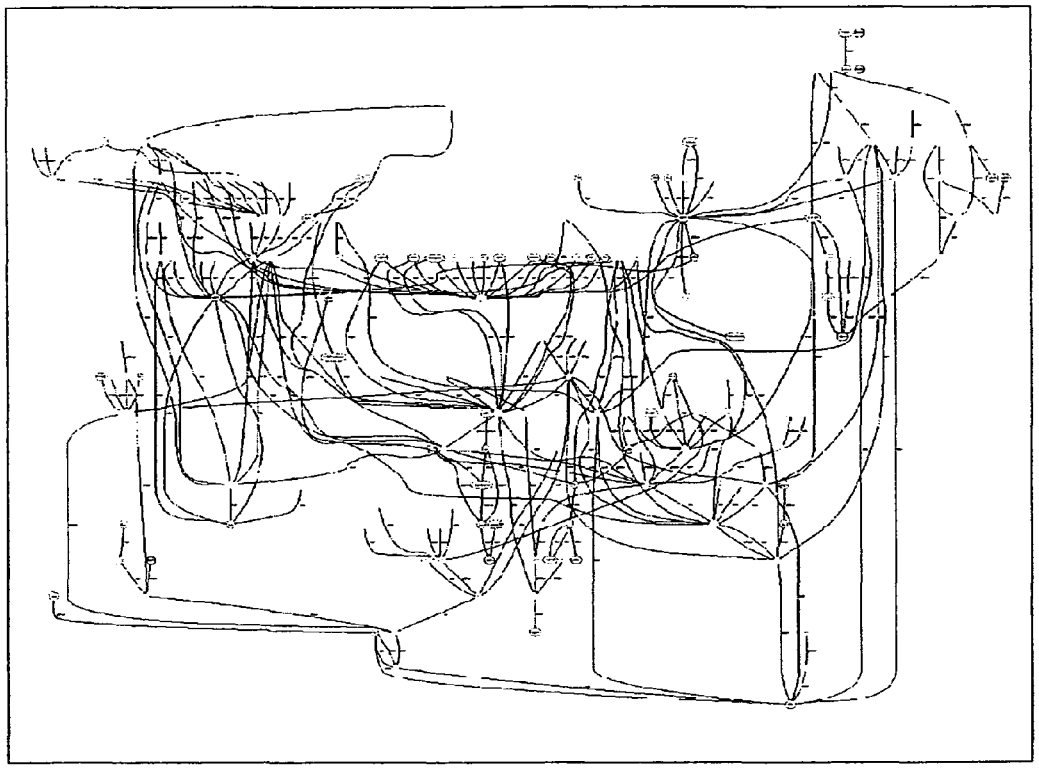
Figure 11:
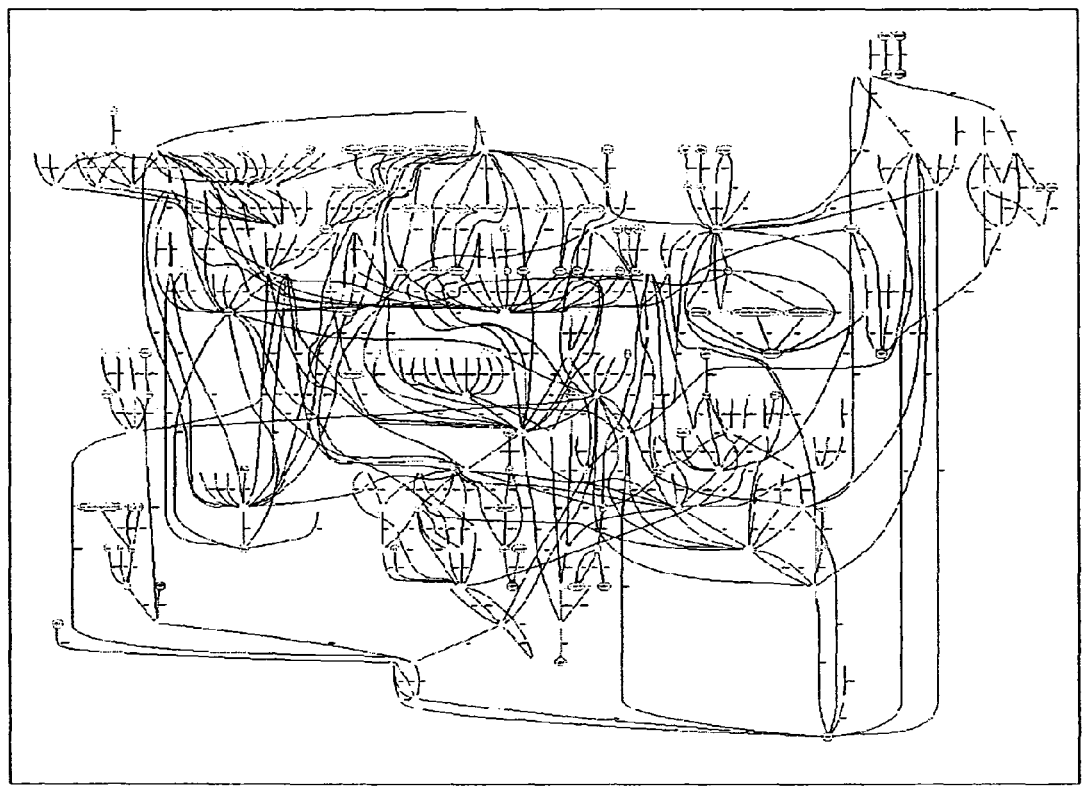

The matrix method is another way of studying the changes in a knowledge graph. Given a list of nodes of interest (e.g., statistically significant, highly modulated RNA in an experiment) the nodes are placed in a matrix with each node placed as an entry in a column and a row. The shortest path is then generated for every pair of nodes (redundant pairings are ignored). All the generated pathways are then merged as explained above. The matrix method can also be applied by not only finding one path for each cell in the matrix, but by generating multiple pathways. This can be done in several ways: (1) generating all pathways for each pair; (2) generating the top "n" pathways starting with the shortest or longest; and (3) generating all the top "n" pathways that are no more than some pre-determined number of steps long. The matrix method also is useful in determining how a set of biological entities are related to one another. FIG. 5 shows the result of a matrix method analysis among three nodes, "Acox1", "LDL" and "FXR" after merging all of the shortest paths between each pair of nodes.

Logical Simulation

Logical simulation may also be utilized in accordance with the invention. Logical simulation refers to a class of operations conducted on a knowledge base wherein observed or hypothetical changes are applied to one or more nodes in the knowledge base and the implications of those changes are propagated through the network based on the causal relationships expressed as assertions in the knowledge base.

A logical simulation can either be forward, where the effects of changes are inferred and are propagated downstream from the initial points of change, or it can be backward where the possible causes are inferred and are propagated upstream from the initial points of change. In either case, one result of a logical simulation is a new, derived network, comprised of the nodes and assertions that were involved in the propagation of cause or effect. This derived network embodies a hypothesis about the system being studied.

Logical simulation includes backward logical simulations, which proceed from a selected node by traversing relationship descriptors which express causal relationships between biological elements. The simulation is "backwards" when relationship descriptors are traversed such that the simulation moves from a selected node to nodes which, if perturbed, could cause perturbation in the selected node. As the backward simulation progresses it identifies the set of nodes and relationships which, if perturbed, may hypothetically be responsible for the experimentally observed changes in the biological system. In short, this computation answers the question "What could have caused the observed change?"

Logical simulation also includes forward logical simulations, which also proceed from a selected node by traversing relationship descriptors which express causal relationships between biological elements. The simulation is "forwards" when relationship descriptors are traversed such that the simulation moves from a selected node to nodes which could be perturbed if the selected node is perturbed. As the forward simulation progresses it identifies the set of nodes and relationship descriptors which may hypothetically be perturbed by the perturbation of the selected node. In short, this computation answers the question, "What are the possible effects of this change?" The sets of nodes and relationship descriptors derived by these two methods comprise connected graphs which may be also described as sets of "causal paths," chains of causal relationships connecting nodes. Each unique causal path identified by either forward logical simulation or backward logical simulation may be considered a hypothesis, a hypothesis that perturbations in the first node in the path may cause perturbations in the last node in the path via perturbations in the intervening nodes.

The invention provides methods for performing a logical simulation on a hypothetical perturbation. One or more nodes may be selected and specified as perturbed, regardless of whether they are observed in an actual experiment. Backward logical simulation on the hypothetical perturbation identifies the nodes and relationship descriptors which, if perturbed, would potentially explain the hypothetical perturbation. Forward logical simulation on the hypothetical perturbation identifies the nodes and relationship descriptors which would potentially be perturbed due to the hypothetical perturbation.

The invention provides methods for performing a logical simulation between at least two groups of selected nodes. One group is designated "source nodes" and the other may be designated "target nodes." Backward simulation may be performed starting from the target nodes, finding all causal paths which connect from the source nodes to the target nodes. Alternatively, forward simulation may be performed starting from the source nodes, finding all causal paths which connect from the source nodes to the target nodes. The set of these paths, derived in either manner, comprise the set of all possible explanations for perturbations of the target nodes which could hypothetically be caused due to perturbations of the source nodes.

Referring again to FIG. 1, for example, in the case of a backward simulation based on observed changes in RNA expression levels, FIG. 1 shows paths of inference to find upstream causes starting with an observed change in mRNA levels for a particular gene. One specific chain of causation could be as follows: a phosphorylation of a transcription factor by a kinase such that the kinase changes the activity of the transcription factor can in turn induce changes in the expression of genes controlled by that transcription factor. This diagram provides a "pseudo code" description of the inferences that are then performed to find possible causes of each of the observed RNA changes. The types of assertions to be explored are not limited to those in this diagram. Any assertion in the knowledge base that represents a causal biological linkage may be included in this type of analysis. In turn, each of the possible causes may then be explored to find their respective possible causes. The process may be repeated for as many steps as desired, annotating nodes in the knowledge base or assembly according to their possible role in the causation of the observed changes.

The resulting derived network embodies a hypothesis about the possible causes of the observed data. Moreover, depending on the methods of propagation of causality, it may further be considered a hypothesis about the most implicated and most consistent possible causes of the observed data, i.e. a set of possible causes ranked by objective criteria. This technique is not limited to RNA expression data, but rather may work with any set of changes that can be expressed in the representation system, including but not limited to proteometric data, metabolomic data, post-translational modification data, or even reaction rate data.

Logical simulation using the invention may also be applied to analyze the possible pathways between a single source node and a single target node; furthermore, the invention may be applied to multiple source nodes and/or multiple target nodes in a single logical simulation. A logical simulation may be applied to specified class(es) of nodes or of relationship descriptors. The logical simulation may also specify the exclusion of specified node(s), relationship descriptor(s), or classes of nodes or descriptors. For example, the search may specify that the logical simulation only traverse relationship descriptors relating to genes. Alternatively, the search may be limited to relationship descriptors relating to proteins, the expression of proteins, or the transcription of an mRNA to a protein.

The invention, in another aspect, includes a search that further limits the available nodes or relationship descriptors for a particular logical simulation. For example, according to one embodiment, the search may exclude specific nodes, requiring the logical simulation to connect the source and target node in a path that does not include the specified nodes. Alternatively, according to another embodiment, the search may require specific nodes, requiring the logical simulation to connect the source and target node in a path that contains the specified nodes. The search may also take the form of a negative test, requesting the logical simulation to find a pathway (or the absence of a pathway) beginning at a source node that does not connect to the target node in a specified number of steps. The search may also request the shortest path between the source and target nodes. Further, the logical simulation may be limited to a single direction, only allowing traversal of relationship descriptors in a single specified direction, either upstream or downstream, from the selected starting node.

The goal of the present invention is to find a cause or source of changes induced by a perturbation to a biological system. Perturbations are induced, for example, by a disease, toxicity, environmental exposure, abnormality, morbidity, aging, or other stimulus. The invention is based on the premise that perturbations to a biological system can be analyzed for the effects they may cause downstream in a biological system or for the cause of the perturbation upstream within the biological system. Based on existing or future knowledge about biological elements and the relationships between elements, perturbations to nodes or relationships are traversed within the knowledge base to discern their causes and effects. Changes in the amount, character, or quality of a biological element such as a molecule of RNA, a protein, a metabolite or another known element, can be evaluated to determine their possible cause. For example, if the level of a particular molecule of RNA is observed to increase in a particular diseased tissue versus the same healthy tissue, the RNA molecule can be evaluated to discern factors that have the potential to control the level of the RNA molecule.

The process of traversing backwards through relationships in the knowledge base can be applied iteratively from each subsequent change to yield a tree-like structure of interactions and possible causes. Metrics are applied to the results to find areas of commonality among the observations. These common areas are highlighted as areas of control for the network and can be further evaluated by biological experimentation to determine if the hypothesized cause or effect is observed in an actual biological system.

The relationships traversed during an evaluation of a biological perturbation represent facts relating existing objects in a system, or a fact about one object in the system and some literal value, or any combination thereof. In various embodiments, relationship descriptors may represent knowledge such as the effect of an increase or decrease in the level of RNA, protein, or a metabolite. The level of an RNA molecule, for example, may increase or decrease because the transcription factor that controls the RNA is either up or down, either activated or deactivated, or is not being degraded by some other molecule. Alternatively, the RNA level may change because it is either being degraded more or degraded less, or because it is being transported in or out of the system at a different rate.

The level of a protein, for example, may increase or decrease because the RNA that codes for the protein is up or down, its promotor is up or down, the protein is being degraded either faster or slower, it is being transported differently, it is complexing with something else that is either up or down, it is unable to complex with what it usually complexes, or it is being or not being phosphorylated or acylated as usual.

The level of a metabolite, for example, may increase or decrease because the biochemical reaction that makes the metabolite could be altered, the enzyme could be upregulated or downregulated or activated or deactivated, the substrates could be up or down, the environmental conditions for the reaction may be up or down, or the transport and or secretion of the metabolite may be up or down. The forgoing examples are meant to be illustrative and are not a complete recitation of the possible relationships described in the global knowledge base.

To analyze changes in a biological network induced by a perturbation, relationship descriptors (describing relationships such as those discussed above) are traversed to generate a list of possible causes. The relationship descriptors for each identified cause are then traversed and the process repeated a specified number of steps until a web of relationships is developed. For example, if the level of an RNA molecule is increased in a biological system, one possible cause is that its transcription factor is increased. If the transcription factor is a protein, the relationship descriptors regarding proteins can be traversed to analyze possible biological elements or relationships causing the protein level to increase. The relationships can be additionally be traversed for a desired number of subsequent steps to generate a causal tree.

In one embodiment of the invention, a biological relationship in a biological system is hypothesized using a software implemented method. A knowledge base, such as a database of biological knowledge, is provided comprising a multiplicity of nodes representative of biological elements and relationship descriptors, which represent relationships between specific nodes or properties of the nodes. A relationship descriptor may describe, for example, the condition, source, amount, or substructure of a molecule. It may also describe, for example, an aspect of a biological structure, physiological condition, trait, phenotype, biological process, clinical data, medical data, or disease data and chemistry. A relationship descriptor may correspond to an epistemological relationship between a pair of nodes. A relationship descriptor may also comprise a case frame, as described above.

According to the invention, a target node is selected from the knowledge base for investigation. In one embodiment, the target node is known from experimental observation to correspond to a biological element and the biological element is known to increase in number or concentration, decrease in number or concentration, appear within, or disappear from a real biological system when that system is subjected to a perturbation.

Starting at the selected target node, a logical simulation is performed backward within the knowledge base from the target node, through a path of relationship descriptors describing potentially causative nodes to discern a source node hypothetically responsible for the experimentally observed change in the selected target node.

In one embodiment of the invention, the hypothetically responsible source node is then selected for simulated perturbation. Starting at the selected hypothetically responsible source node, a logical simulation is performed forward within the knowledge base from the hypothetically responsible source node, through a path of relationship descriptors describing potentially affected nodes to discern the extent to which the simulated perturbation of the hypothetically responsible source node generates the experimentally observed change in the target node.

In another embodiment of the invention, a perturbation to a selected target node is specified. The perturbation may be known or may not be known from experimental observation to correspond to a biological element or to correspond to a perturbation of that biological element. The perturbation comprises an effective increase in concentration or number, stimulation of activity, an effective decrease in concentration or number, inhibition of activity, or the appearance or disappearance of the target node.

According to this embodiment, a logical simulation is performed within the knowledge base from the selected target node, through the relationship descriptors, upstream along a path defined by nodes which affect the state of the target node directly or indirectly to discern a hypothesis potentially explanatory of a cause of the specified change in the target node within the system. In another embodiment of this invention, the logical simulation is performed within the knowledge base from the selected target node, through the relationship descriptors, upstream along a path defined by nodes which affect the state of the target node directly or indirectly to discern a node hypothetically responsible for the specified change in the target node.

Alternatively, according to this embodiment, a logical simulation is performed within the knowledge base from the selected target node, through the relationship descriptors, downstream along a path defined by nodes affected by the target node directly or indirectly to discern a hypothesis potentially explanatory of an effect of the specified change in the target node within the system. In another embodiment of this invention, the logical simulation is performed within the knowledge base from the selected target node, through the relationship descriptors, downstream along a path defined by nodes affected by the target node directly or indirectly to discern a node hypothetically affected by the specified change in the target node.

In one embodiment of the invention, the hypothetically responsible source node is then selected for simulated perturbation. Starting at the selected hypothetically responsible source node, a logical simulation is performed backward within the knowledge base from the hypothetical source node, through a path of relationship descriptors describing potentially affecting nodes to discern the extent to which the simulated perturbation causes the specified change in the target node.

In another embodiment of the invention, the target node is then selected for simulated perturbation. Starting at the target node, a logical simulation is performed forward within the knowledge base from the target node, through a path of relationship descriptors describing potentially affected nodes to discern the extent to which the simulated perturbation generates the hypothesized effects of the specified change in the target node.

According to one embodiment of the invention, at least a pair of target nodes are selected from the knowledge base. A logical simulation is performed within the knowledge base between the target nodes, through relationship descriptors along a path defined by at least one potentially causative node or at least one potential effector node to discern one or a group of pathways hypothetically linking the selected target nodes. A logical simulation may be performed within the database upstream, along a path defined by nodes affecting the state of the target node directly or indirectly to discern hypotheses starting at the target node, each of which is potentially explanatory of a cause of the specified change in the target node within the system or hypothetically responsible for the specified change in the target node. A logical simulation may also be performed within the database downstream, along a path defined by nodes affected by the target node directly or indirectly to discern hypotheses potentially explanatory of an effect of a specified change in the target node within the system or hypothetically affected by the specified change in the target node. The result of the logical simulation may be the determination of a group of pathways hypothetically linking the two or more target nodes by chains of causal mechanism.

In another embodiment, one node of the pair of nodes is then selected for perturbation. Starting at the virtually perturbed node, a logical simulation is then performed forward within the knowledge base, through a path of relationship descriptors describing potentially affected nodes to discern the extent to which the simulated perturbation generates a predicted effect on the other node of the pair of nodes.

In various embodiments, the invention includes method steps, applications, and devices wherein the database contains noisy data, erroneous data, or omits nodes representing structures, processes, or networks present in the real biological system. A knowledge base may be augmented by insertion of new nodes and relationship descriptors derived from the knowledge base or may be filtered by excluding subsets of data based on other biological criteria. The granularity of the system may be increased or decreased as suits the analysis at hand (which is critical to the ability to make valid extrapolations between species or generalizations within a species as data sets differ in their granularity). A knowledge base may be made more compact and relevant by summarizing detailed knowledge into more conclusory assertions better suited for examination by data analysis algorithms, or better suited for use with generic analysis tools, such as cluster analysis tools.

A knowledge base may be updated periodically as knowledge advances, and the respective evolving knowledge base can be saved to show the progression of knowledge in the area. A knowledge base may be augmented in various ways, including having a curator add new data from a structured or unstructured database or add data derived from literature. A knowledge base also may be incorporated back into a global repository so that new assertions may be used as raw material for creation of a different assembly.

In various embodiments, the invention includes method steps, applications, and devices wherein a probability algorithm is applied to plural hypotheses to assess which hypothetical relationship has the highest probability of representing real biology. In one embodiment, the probability algorithm evaluates a hypothesis and assigns that hypothesis a score based on the number of predicted, number of observed, and number of contrary outcomes. The algorithm calculates a concurrence of events (the number of correct/incorrect outcomes compared to chance) and a measure of richness (statistical significance compared to random) for each measurement. The probability is the product of the concurrence and richness scores. The probability scores for two hypotheses are compared to determine which hypothetical relationship has the highest probability of representing real biology. The pathway outcomes for two related factors may also be compared to determine which nodes and relationship pathways are unique to each factor and where their paths overlap. Additionally, multiple pathway outcomes may be ranked in order of the probability that they represent real biology based on a parameter of consistency or explanatory power. Examples of parameters include the probability, concurrence and richness scores.

In various embodiments, the invention includes method steps, applications, and devices wherein the biological system is a mammalian biological system. The method further comprises determining the identity of a second hypothetically responsible node upstream of the hypothetically responsible node. The second node is predicted to induce a predetermined change in the biological system upon inhibition or stimulation.

In various embodiments, the invention includes method steps, applications, and devices for conducting an experiment on a biological specimen to determine if the hypothetical relationship predicted by the logical simulation corresponds to the biologically observed change. The invention includes performing an experiment on a biological specimen to attempt to induce the observed change.

In various embodiments, the invention includes method steps, applications, and devices wherein the biological system being analyzed is a mammalian biological system that is perturbed from stasis. The perturbation is induced by a disease, toxicity, environmental exposure, abnormality, morbidity, aging, or another stimulus.

In various embodiments, the invention includes method steps, applications, and devices for determining the state of a group of nodes reproducibly associated with the biological state of the mammal which can act as a marker set characteristic of the biological state.

In various embodiments, the new biological knowledge produced by the method includes predictions of physiological behavior in humans, for example, from analysis of experiments conducted on animals, such as drug efficacy and/or toxicity, or the discovery of biomarkers indicative of the prognosis, diagnosis, drug susceptibility, drug toxicity, severity, or stage of disease.

The invention provides computing devices for analyzing a biological knowledge base and for discovering new biological knowledge. The computing devices include means for accessing an electronic database of biological assertions comprising a multiplicity of nodes representative of biological elements, and relationship descriptors describing relationships between nodes and properties of nodes, and a user interface for specifying biological elements or perturbations which will be analyzed by the device. The devices also include a computer application to perform a logical simulation of a perturbation to a selected biological element or relationship, to analyze the source or effects of the perturbation, and to assess the probability that the simulation generated pathway represents real biology. The invention also provides articles of manufacture having a computer-readable program carrier with computer-readable instructions embodied thereon for performing the methods and systems described above.

Example 1

Figure 12A:
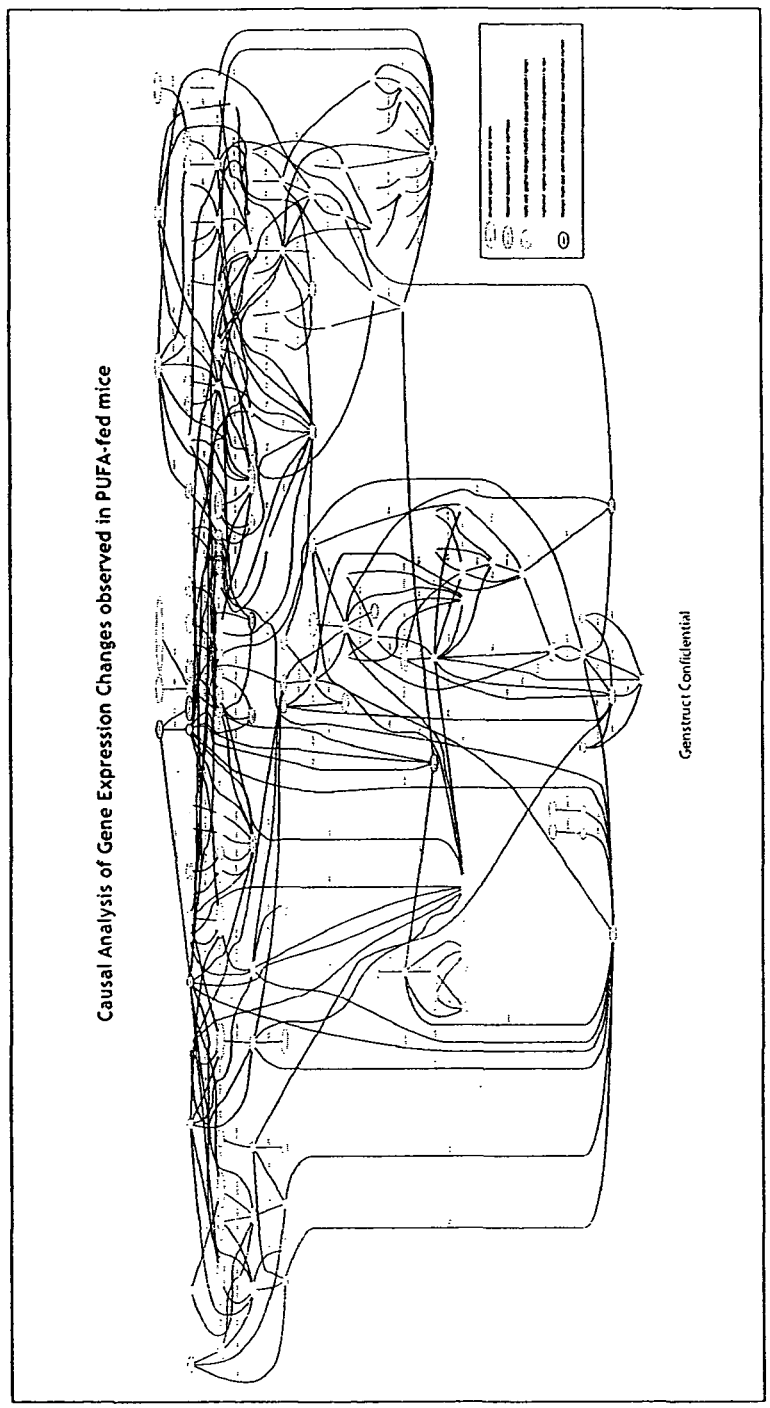
FIG. 12A shows an explanation diagram in accordance with an illustrative embodiment of the invention.
Figure 12B:
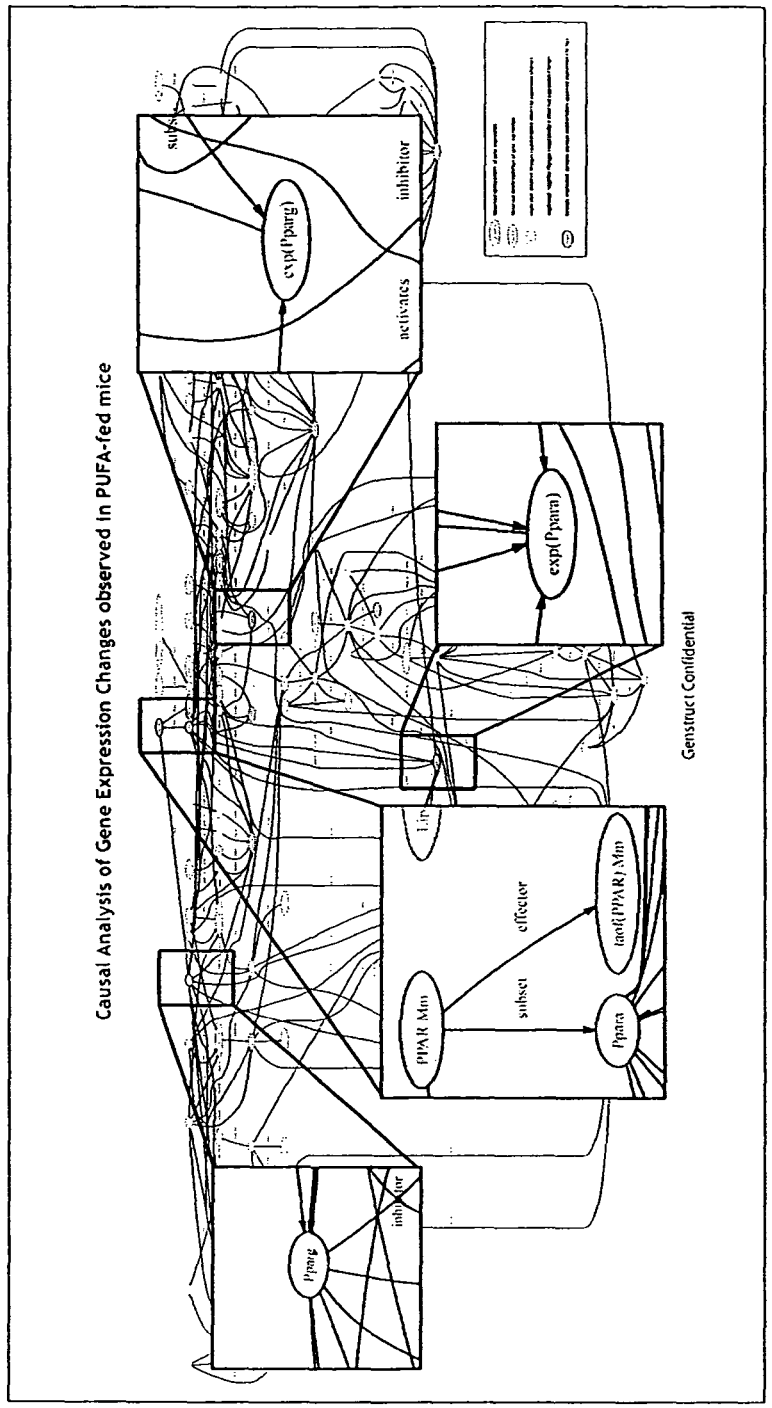
FIG. 12B shows a detail of the explanation diagram in FIG. 12A in accordance with an embodiment of the invention.

An example of an embodiment of the invention, examining liver changes in mice fed with polyunsaturated fatty acid (PUFA) rich foods, is described below and shown in FIGS. 6 through 11. This example application was conducted using publicly available results from Berger et al., Dietary effects of arachidonate-rich fungal oil and fish oil on murine hepatic and hippocampal gene expression, Metabolic and Genomic Regulation, Nestle Research Center, Switzerland. The research looked at mouse liver changes on a diet rich in polyunsaturated fatty acid in fungal and fish oils. We used differential gene expression data in our model of dyslipidemia and had the system work backwards from the data to find the most likely causes of observed changes. FIGS. 6 through 11 are illustrations of how the system walked backwards from a few selected genes (6 in this case). At each stage, the system walks an extra step backwards to find possible causes. As shown in FIGS. 12A and 12B, the area with the best score was PPAR.

FIG. 12A shows an explanation diagram of how PPAR is connected to a phenotype of interest. This diagram was generated after doing the back simulation in which PPAR was identified as the cause or area of control. Links were then extracted from the knowledge base that corresponded to the path that the back simulator took to get to PPAR. FIG. 12B, which is a zoomed in version of FIG. 12A, shows the user the exact links (an explanation) of how the system concluded PPAR was the cause or area of control. This was done by keeping track of the nodes and links that were traversed by the backwards simulator as it worked its way through the network and then displaying the nodes and links that led to a specific consensus area. While the result of this example was obtained algorithmically by the present invention, Berger et al. also reached a similar conclusion in their research.

Figure 13:
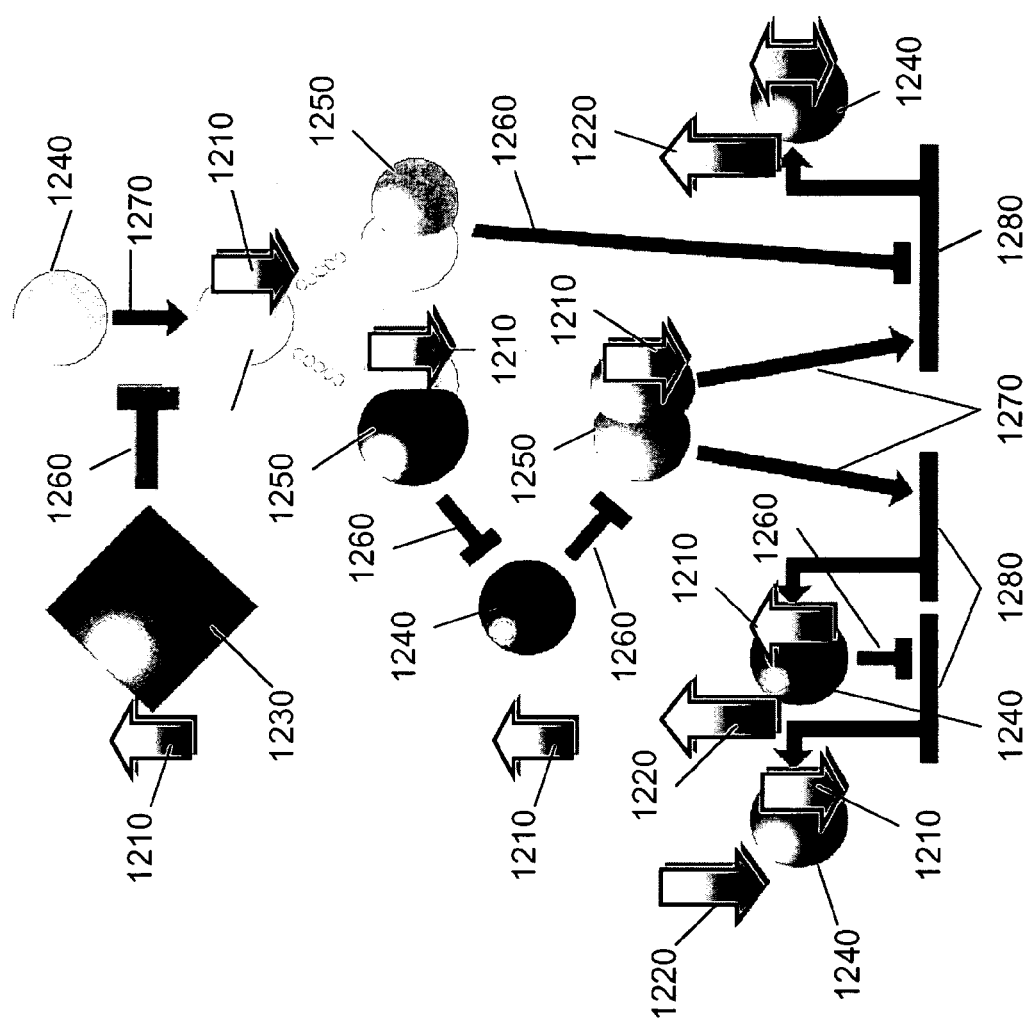
FIG. 13 is a diagram showing propagation of predicted changes in a forward simulation being compared with observed expression changes in accordance with an illustrative embodiment of the invention.

FIG. 13 is a manually composed diagram which shows propagation of predicted changes 1210 in a forward simulation being compared with observed expression changes 1220. This diagram illustrates the propagation of predicted protein changes 1210 based on an increase in the amount of a compound 1230 through a known pathway. In this diagram, spheres 1240 represent proteins. Pairs of adjacent spheres 1250 indicate complexes of proteins. Thin arrows with T-shaped heads 1260 indicate inhibitions or causal decreases. Thin arrows with pointed heads 1270 indicate an activation or causal increase. Gene expression relationships are indicated by the arrows 1280. The diagram is intended to clarify the way in which changes predicted by a hypothesis may be compared with observed data.

Figure 14:
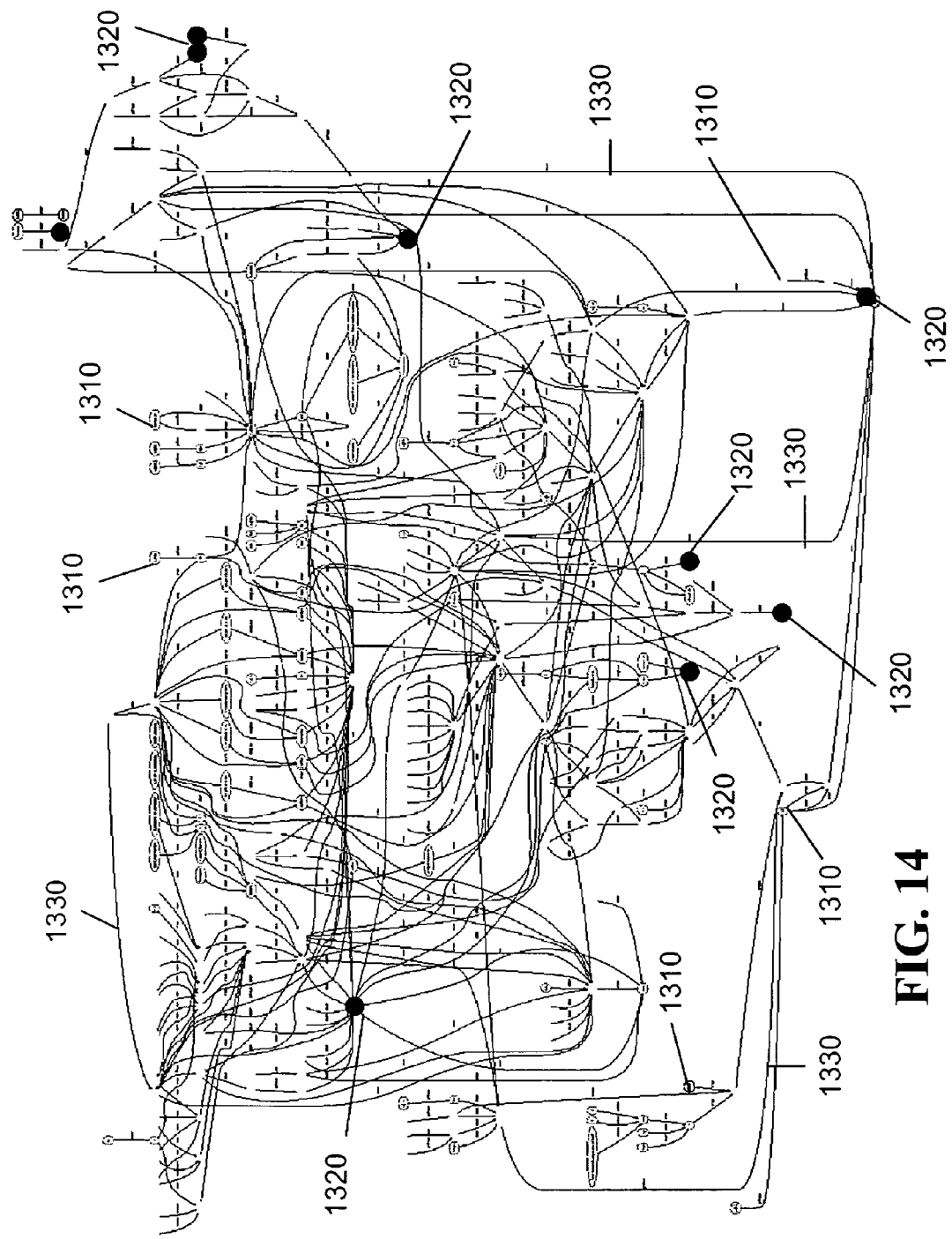
FIG. 14 is a diagram generated by a backward simulation from nine expression data points, followed by pruning of the graph to show only the chains of reasoning which support the primary hypotheses, in accordance with an illustrative embodiment of the invention.

FIG. 14 is a diagram generated by backward simulation from nine observed expression data points 1320, followed by pruning of the graph to show only the connections 1330 which support the primary hypotheses. Each node 1310 in this figure represents either a gene, protein, or compound. Nine of these nodes 1320 represent changes in expression of genes in response to dietary polyunsaturated fatty acids. The rest of the diagram is generated by exploring the knowledge base or assembly to find possible nodes 1310, which if changed, could explain one or more of the observed nine changes 1320 and then removing nodes 1310 and connections 1330 such that only the best explanations are shown.

One example of a method comprised of techniques herein above would be as follows: (1) load a set of expression fold-change data to the assembly; (2) run a backward logical simulation based on the fold-change data; (3) examine the resulting derived network and choose the most implicated nodes—the ones which are the highest ranking possible causes of the observed data; (4) for that set of nodes, return to the original assembly and run a pathfinding algorithm to find the derived network which is the minimal graph connecting the nodes; and (5) output the resulting derived network as a graph. Methods such as this example can be embodied as functions in the programming framework and can be named and re-used.

FIG. 15 illustrates a visualization technique comprising an aspect of the present invention that is based on a forward simulation that compares predicted outcomes with actual laboratory data. This diagram shows the direct downstream effects of a perturbation. The right-most column shows the expected outcome of a perturbation in the system. Each predicted value is compared to the actual values to determine how closely the predictions explain the lab data. A correlation can be calculated between the predicted outcome and the actual effect of each treatment. In FIG. 15, the cells marked with horizontal lines show a significant increase, the cells marked with vertical lines show a significant decrease, the darkened cells show no change, and the undarkened cells are insignificant. Perturbations may include, but are not limited to, the increase or decrease in concentration of a transcription factor, a small molecule, or a biochemical catalyst.

Applications of the invention include, but are not limited to, mechanisms of action (observations of tissue with and without drug can help elucidate the area in which the drug is working), mechanism of resistance (observations on the differences between responders and non-responders to a drug can lead to consensus areas that are the root cause(s) of resistance to treatment), mechanism of disease (observations of diseased versus healthy tissue(s) or patient(s) can lead to mechanisms of disease), and pathway identification (the method can be used to show which pathways are changing in an experiment and can help explain the observations).

Logical simulations, in an alternative embodiment, are performed within an assembly. Assemblies refer to sub-knowledge bases and derived knowledge bases. These specialty knowledge bases can be constructed from a global knowledge base by extracting a potentially relevant subset of life science-related data satisfying criteria specified by a user as a starting point, and reassembling a specially focused knowledge base having the structure disclosed herein. Assemblies are described in detail in co-pending, co-owned U.S. patent application Ser. No. 10/794,407, the disclosure of which is incorporated by reference herein.

Assemblies may be used to implement logical simulations, to evaluate data sets not present in a global repository at the time of the original assembly construction (e.g., to retest a hypothesis based on new experimental data), to hypothesize pathways and discern complex and subtle cause and effect relationships within a biological system, and to discern disease etiology, understand toxic biochemical mechanisms, and predict toxic response.

Logical simulations, in another example, are performed on data generated by an epistemic engine. Epistemic engines are described in detail in co-pending, co-owned U.S. patent application Ser. No. 10/717,224, the disclosure of which is incorporated by reference herein. Epistemic engines are programmed computers that accept biological data from real or thought experiments probing a biological system, and use them to produce a network model of protein interactions, gene interactions and gene-protein interactions consistent with the data and prior knowledge about the system, and thereby deconstruct biological reality and propose testable explanations (models) of the operation of natural systems. The engines identify new interrelationships among biological structures, for example, among biomolecules constituting the substance of life. These new relationships alone or collectively explain system behavior. For example, they can explain the observed effect of system perturbation, identify factors maintaining homeostasis, explain the operation and side effects of drugs, rationalize epidemiological and clinical data, expose reasons for species success, reveal embryological processes, and discern the mechanisms of disease. The programs reveal patterns in complex data sets too subtle for detection with the unaided human mind. The output of the epistemic engine permits one to better understand the system under study, to propose hypotheses, to integrate the system under study with other systems, to build more complex and lucid models, and to propose new experiments to test the validity of hypotheses.

In some embodiments, a knowledge base may take the form of one or more database tables, each having columns and rows. It should be understood that a knowledge base or assembly in the form of a database is only one way in which information may be represented in a computer. Information could instead be represented as a vector, a multi-dimensional array, a linked data structure, or many other suitable data structures or representations.

Graphical Output Techniques

A knowledge base, pathway, or group of pathways can be displayed visually as a graph of nodes connected by connections representing biological relationships between and among nodes. These graphs can be inspected by a scientist to understand the biological system and to facilitate the discovery of new biological knowledge about life sciences-related systems. Using these tools to discern biologically relevant insights into how a system behaves can be extremely valuable in drug research and development, and for developing a variety of therapies. Visualization techniques can also be used to display knowledge and associated data to enhance user understanding and recognition of relationships among entities that may emerge as patterns and clusters Apparatus The functionality of the systems and methods disclosed herein may be implemented as software on a general purpose computer. In some embodiments, a computer program may be written in any one of a number of high-level languages, such as FORTRAN, PASCAL, C, C++, LISP, JAVA, or BASIC. Further, a computer program may be written in a script, macro, or functionality embedded in commercially available software, such as EXCEL or VISUAL BASIC. Additionally, software could be implemented in an assembly language directed to a microprocessor resident on a computer. For example, software could be implemented in Intel 80×86 assembly language if it were configured to run on an IBM PC or PC clone. Software may be embedded on an article of manufacture including, but not limited to, a storage medium or computer-readable medium such as a floppy disk, a hard disk, an optical disk, a magnetic tape, a PROM, an EPROM, or CD-ROM.

EXAMPLE

Validation Algorithm for Biological Models

An example of an algorithm for use in validating a biological model by comparing predicted to actual results is described below and in the pseudo code in FIG. 16. This algorithm assumes that there exists a knowledge base representing a biological system with data from gene expression experiments mapped onto the knowledge base.

The predicted results can be determined in two stages. First, a backward simulation as described herein is run on a knowledge base to determine potential causes of the gene expression changes. The backward simulation produces a list of genes and a score for each. The score for each node is based on the "votes" it received during the backward simulation. At the beginning of the backward simulation, nodes representing genes which are significantly upregulated are assigned positive votes, while those which are significantly downregulated are assigned negative votes. During the simulation, votes are copied from node to node according to a set of rules which follow the causal relationships expressed in the knowledge base. At the end of the simulation, the score for each node is computed as a set of three numbers: the sum of positive votes, the sum of negative votes, and an overall score, which is the sum of the positive and negative votes. At this point, the set of nodes representing potential causes ("the causes") may be used for the next step and may be selected based on each node's score, or the set of potential causes may be determined manually. In the second stage, the votes for all nodes are set to zero and a forward simulation as described herein is run on the selected set of causes. The votes are handled in the same way, except that they are propagated from causes to potential effects. At the end of the forward simulation, nodes which represent the expression of genes are reviewed. Those with a positive overall score are the ones which the forward simulation predicts to be up-regulated and those with a negative overall score are the ones which are predicted to be down-regulated. The results of the forward simulation represent the overall predicted results.

The actual results are classified into two categories based on the gene expression data. One list contains up-regulated genes and another list contains down-regulated genes. The genes included in these lists can be generated by various statistical methods, taking into account the absolute magnitude of the change (e.g., signal level), the relative magnitude of the change (e.g., fold values), statistical significance, etc. Alternatively, the genes may be selected manually.

After the predicted and actual results have been generated, overall results for each gene in the following three cases are tabulated. In the first case, a gene is predicted to be up-regulated. If the gene is in the actual list of up-regulated genes, the "correct prediction counter" is incremented. Otherwise, if the gene is in the actual list of down-regulated genes, the "opposite prediction counter" is incremented. If the gene is not in either list of actual gene expression changes, then the "predicted but not observed counter" is incremented. In the second case, a gene is predicted to be down-regulated. If the gene is in the actual list of up-regulated genes, the "opposite prediction counter" is incremented. Otherwise, if the gene is in the actual list of down-regulated genes, the "correct prediction counter" is incremented. If the gene is not in either list of actual gene expression changes, then the "predicted but not observed counter" is incremented. In the third case, there is no prediction for the gene and the "no net change counter" is incremented.

For every gene that is either in the actual up-regulated or down-regulated gene lists, but does not have any predictions, the "observed not predicted counter" is incremented. The five "counters" are then outputted: (1) "correct prediction counter", (2) "opposite prediction counter", (3) "predicted but not observed counter", (4) "observed not predicted counter", and (5) "no net change counter". These counters may be visualized, for example, in a histogram format, or pie chart format. Such visualizations provide an intuitive means for a scientist to initially assess the degree to which the generated hypothesis matches the observed data.

While the invention has been particularly shown and described with reference to specific embodiments and illustrative examples, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. Apparatus for hypothesizing a biological relationship, comprising:

a processor;

an electronic data store holding a database comprising a multiplicity of nodes representative of biological elements, and relationship descriptors describing causal relationships between nodes, the causal relationships defining how an increase or decrease in activity or abundance of one node has been shown, or is suspected, to cause an increase or decrease in the activity or abundance of another node, the database being non-specific in that at least some relationship descriptors define casual relationships that are not known or suspected to be relevant to any particular biological context of interest; and computer memory holding computer program instructions which, when executed by the processor, hypothesize the biological relationship from the collection of non-specific relationship descriptors by executing one of: a reverse logical simulation, and a forward logical simulation, the computer program instructions executable:

(a) for a reverse logical simulation: (i) to select a set of target nodes; (ii) to associate to the set of target nodes a set of perturbations, wherein each target node of the set of target nodes has an associated perturbation, and wherein the set of perturbations represent one of: experimentally-observed perturbations and theoretical perturbations; (iii) with respect to at least one particular source node that is hypothetically responsible for the set of perturbations, to traverse causal relationships in the database in a reverse direction, from an effect to a cause of each causal relationship, to identify a set of one or more paths from each of the target nodes back to the particular source node, the set of paths comprised of casual relationships of which at least one such causal relationship is not known or suspected to be relevant to the particular biological context of interest; (iv) based on results obtained from the traversing step, to define, as a hypothesized biological relationship, the particular source node, together with the one or more casual relationships that comprise the set of paths that link the particular source node to the set of target nodes; and (v) to compute one or more scores associated with the hypothesized biological relationship based on the set of perturbations and the set of paths;

(b) for a forward logical simulation: (i) to select a set of source nodes; (ii) to associate to the set of source nodes a set of perturbations, wherein each source node of the set of source nodes has an associated perturbation, and wherein the set of perturbations represent one of: experimentally-observed perturbations and theoretical perturbations; (iii) with respect to at least one particular target node, to traverse causal relationships in the database in a forward direction, from a cause to an effect of each causal relationship, to identify a set of one or more paths from each of the source nodes forward to the particular target node, the set of paths comprised of casual relationships of which at least one such causal relationship is not known or suspected to be relevant to the particular biological context of interest; (iv) based on results obtained from the traversing step, to define, as the hypothesized biological relationship, the particular target node, together with the one or more casual relationships that comprise the set of paths that link the particular target node to the set of source nodes; and (v) to compute one or more scores associated with the hypothesized biological relationship based on the set of perturbations and the set of paths.

2. The apparatus as described in claim 1 wherein in the reverse logical simulation the set of paths that link the particular source node to the set of target nodes includes zero or more additional nodes that are other than the particular source node and the set of target nodes and that lie along a path of the set of paths.

3. The apparatus as described in claim 1 wherein in the forward logical simulation the set of paths that link the particular target node to the set of source nodes includes zero or more additional nodes that are other than the particular target node and the set of source nodes and that lie along a path of the set of paths.

4. The apparatus as described in claim 1 wherein the reverse or forward logical simulation is initiated from a subset of the database.

5. An article comprising a tangible machine readable medium that stores a program, the program being executable by a machine to perform a method for hypothesizing a biological relationship from biological information in a database, the database comprising a multiplicity of nodes representative of biological elements, and relationship descriptors describing causal relationships between nodes, the causal relationships defining how an increase or decrease in activity or abundance of one node has been shown, or is suspected, to cause an increase or decrease in the activity or abundance of another node, the database being non-specific in that at least some relationship descriptors define casual relationships that are not known or suspected to be relevant to any particular biological context of interest, the method comprising:

hypothesizing the biological relationship from the collection of non-specific relationship descriptors by executing one of: a reverse logical simulation, and a forward logical simulation, wherein:

(a) for a reverse logical simulation, the method is operative: (i) to select a set of target nodes; (ii) to associate to the set of target nodes a set of perturbations, wherein each target node of the set of target nodes has an associated perturbation, and wherein the set of perturbations represent one of: experimentally-observed perturbations and theoretical perturbations; (iii) with respect to at least one particular source node that is hypothetically responsible for the set of perturbations, to traverse causal relationships in the database in a reverse direction, from an effect to a cause of each causal relationship, to identify a set of one or more paths from each of the target nodes back to the particular source node, the set of paths comprised of casual relationships of which at least one such causal relationship is not known or suspected to be relevant to the particular biological context of interest; (iv) based on results obtained from the traversing step, to define, as a hypothesized biological relationship, the particular source node, together with the one or more casual relationships that comprise the set of paths that link the particular source node to the set of target nodes; and (v) to compute one or more scores associated with the hypothesized biological relationship based on the set of perturbations and the set of paths;

(b) for a forward logical simulation, the method is operative: (i) to select a set of source nodes; (ii) to associate to the set of source nodes a set of perturbations, wherein each source node of the set of source nodes has an associated perturbation, and wherein the set of perturbations represent one of: experimentally-observed perturbations and theoretical perturbations; (iii) with respect to at least one particular target node, to traverse causal relationships in the database in a forward direction, from a cause to an effect of each causal relationship, to identify a set of one or more paths from each of the source nodes forward to the particular target node, the set of paths comprised of casual relationships of which at least one such causal relationship is not known or suspected to be relevant to the particular biological context of interest; (iv) based on results obtained from the traversing step, to define, as the hypothesized biological relationship, the particular target node, together with the one or more casual relationships that comprise the set of paths that link the particular target node to the set of source nodes; and (v) to compute one or more scores associated with the hypothesized biological relationship based on the set of perturbations and the set of paths.

6. The article as described in claim 5 wherein in the reverse logical simulation the set of paths that link the particular source node to the set of target nodes includes zero or more additional nodes that are other than the particular source node and the set of target nodes and that lie along a path of the set of paths.

7. The article as described in claim 5 wherein in the forward logical simulation the set of paths that link the particular target node to the set of source nodes includes zero or more additional nodes that are other than the particular target node and the set of source nodes and that lie along a path of the set of paths.

8. The article as described in claim 5 wherein the reverse or forward logical simulation is initiated from a subset of the database.

9. A method for hypothesizing a biological relationship, comprising:

receiving information from an electronic data store holding a database, the database comprising a multiplicity of nodes representative of biological elements, and relationship descriptors describing causal relationships between nodes, the causal relationships defining how an increase or decrease in activity or abundance of one node has been shown, or is suspected, to cause an increase or decrease in the activity or abundance of another node, the database being non-specific in that at least some relationship descriptors define casual relationships that are not known or suspected to be relevant to any particular biological context of interest; and executing computer program instructions by a machine having a hardware element to hypothesize the biological relationship from the collection of non-specific relationship descriptors by executing one of: a reverse logical simulation, and a forward logical simulation, the computer program instructions executable:

(a) for a reverse logical simulation: (i) to select a set of target nodes; (ii) to associate to the set of target nodes a set of perturbations, wherein each target node of the set of target nodes has an associated perturbation, and wherein the set of perturbations represent one of: experimentally-observed perturbations and theoretical perturbations; (iii) with respect to at least one particular source node that is hypothetically responsible for the set of perturbations, to traverse causal relationships in the database in a reverse direction, from an effect to a cause of each causal relationship, to identify a set of one or more paths from each of the target nodes back to the particular source node, the set of paths comprised of casual relationships of which at least one such causal relationship is not known or suspected to be relevant to the particular biological context of interest; (iv) based on results obtained from the traversing step, to define, as a hypothesized biological relationship, the particular source node, together with the one or more casual relationships that comprise the set of paths that link the particular source node to the set of target nodes; and (v) to compute one or more scores associated with the hypothesized biological relationship based on the set of perturbations and the set of paths;

(b) for a forward logical simulation: (i) to select a set of source nodes; (ii) to associate to the set of source nodes a set of perturbations, wherein each source node of the set of source nodes has an associated perturbation, and wherein the set of perturbations represent one of: experimentally-observed perturbations and theoretical perturbations; (iii) with respect to at least one particular target node, to traverse causal relationships in the database in a forward direction, from a cause to an effect of each causal relationship, to identify a set of one or more paths from each of the source nodes forward to the particular target node, the set of paths comprised of casual relationships of which at least one such causal relationship is not known or suspected to be relevant to the particular biological context of interest; (iv) based on results obtained from the traversing step, to define, as the hypothesized biological relationship, the particular target node, together with the one or more casual relationships that comprise the set of paths that link the particular target node to the set of source nodes; and (v) to compute one or more scores associated with the hypothesized biological relationship based on the set of perturbations and the set of paths.

10. The method as described in claim 9 wherein in the reverse logical simulation the set of paths that link the particular source node to the set of target nodes includes zero or more additional nodes that are other than the particular source node and the set of target nodes and that lie along a path of the set of paths.

11. The method as described in claim 10 wherein in the forward logical simulation the set of paths that link the particular target node to the set of source nodes includes zero or more additional nodes that are other than the particular target node and the set of source nodes and that lie along a path of the set of paths.

12. The method as described in claim 9 wherein the reverse or forward logical simulation is initiated from a subset of the database.

13. The apparatus as described in claim 1 further including program code executed by the processor to apply a probability algorithm to the hypothesized biological relationship to determine if the hypothesized biological relationship has a given probability of representing real biology.

14. The apparatus as described in claim 1 wherein at least one of the set of perturbations is selected to simulate a perturbation suspected to be present in a mammalian biological system when in a state of disease, toxicity, environmental exposure, abnormality, morbidity, aging, or response to other stimulus.

15. The apparatus as described in claim 1, wherein said relationship descriptors comprise descriptors of the condition, location, source, amount, or substructure of a molecule, biological structure, physiological condition, trait, phenotype, biological process, clinical data, medical data, or disease data and chemistry.

16. The apparatus as described in claim 1, wherein one or more relationship descriptors correspond to an epistemological relationship between a pair of nodes.

17. The apparatus as described in claim 1, wherein the database comprises at least 5,000 nodes.

18. The apparatus as described in claim 1, wherein the database comprises at least 10,000 nodes.

19. The apparatus as described in claim 1, wherein the database comprises at least 50,000 nodes.

20. The apparatus as described in claim 1, wherein the comprises at least 100,000 nodes.

21. The apparatus as described in claim 1 wherein the scores associated with the hypothesized biological relationship are based at least in part on the extent to which the nodes within the set of paths affect a specified perturbation in the set of perturbations.

22. The apparatus as described in claim 1 wherein the database further comprises representations of reactions, covalent modification, multi-molecular interactions, transport, catalysis, and inhibition.

23. The apparatus as described in claim 1 further including a display for displaying information associated with the hypothesized biological relationship.

* * * * *